United States Patent
Kesicki

(10) Patent No.: US 12,006,332 B2
(45) Date of Patent: Jun. 11, 2024

(54) AMINOPYRIMIDINE DERIVATIVES AS PHOSPHATIDYLINOSITOL PHOSPHATE KINASE INHIBITORS

(71) Applicant: HiberCell, Inc., New York, NY (US)

(72) Inventor: Edward A. Kesicki, New York, NY (US)

(73) Assignee: HiberCell, Inc., New York, NY (US)

( * ) Notice: Subject to any disclaimer, the term of this patent is extended or adjusted under 35 U.S.C. 154(b) by 0 days.

(21) Appl. No.: 17/576,410

(22) Filed: Jan. 14, 2022

(65) Prior Publication Data

US 2022/0372046 A1     Nov. 24, 2022

Related U.S. Application Data

(63) Continuation of application No. 16/904,073, filed on Jun. 17, 2020, now abandoned.

(60) Provisional application No. 62/862,371, filed on Jun. 17, 2019.

(51) Int. Cl.
| | | |
|---|---|---|
| C07D 498/04 | (2006.01) | |
| C07D 401/14 | (2006.01) | |
| C07D 491/056 | (2006.01) | |
| C07D 498/14 | (2006.01) | |

(52) U.S. Cl.
CPC ......... *C07D 498/14* (2013.01); *C07D 401/14* (2013.01); *C07D 491/056* (2013.01); *C07D 498/04* (2013.01)

(58) Field of Classification Search
CPC .................................................... C07D 498/04
See application file for complete search history.

(56) References Cited

U.S. PATENT DOCUMENTS

| | | | |
|---|---|---|---|
| 5,262,564 A | 11/1993 | Kun et al. | |
| 6,608,052 B2 | 8/2003 | Breitfelder et al. | |
| 6,703,525 B2 | 3/2004 | Kapadia et al. | |
| 7,049,310 B2 | 5/2006 | Burgess et al. | |
| 7,615,643 B2 | 11/2009 | Kuntz et al. | |
| 7,683,064 B2 | 3/2010 | Dewdney et al. | |
| 7,906,509 B2 | 3/2011 | Kennedy-Smith et al. | |
| 8,058,045 B2 | 11/2011 | Collins et al. | |
| 8,124,604 B2 | 2/2012 | Dewdney et al. | |
| 8,153,652 B2 | 4/2012 | Burgess et al. | |
| 8,367,658 B2 | 2/2013 | Collins et al. | |
| 8,445,505 B2 | 5/2013 | Marsilje et al. | |
| 8,618,098 B2 | 12/2013 | Dewdney et al. | |
| 8,703,938 B2 | 4/2014 | Or et al. | |
| 8,759,332 B2 | 6/2014 | Qiu et al. | |
| 8,815,928 B2 | 8/2014 | Or et al. | |
| 8,822,457 B2 | 9/2014 | Dewdney et al. | |
| 8,822,700 B2 | 9/2014 | Qiu et al. | |
| 8,927,709 B2 | 1/2015 | Qiu et al. | |
| RE47,739 E | 11/2019 | Barvian et al. | |
| 11,667,651 B2 | 6/2023 | Lindström et al. | |
| 2005/0101518 A1 | 5/2005 | Solow-Cordero et al. | |
| 2007/0149508 A1 | 6/2007 | Noronha et al. | |
| 2010/0048547 A1 | 2/2010 | Atallah et al. | |
| 2010/0273797 A1 | 10/2010 | Boman et al. | |
| 2011/0172217 A1 | 7/2011 | Fujioka et al. | |
| 2013/0035336 A1 | 2/2013 | Borland et al. | |
| 2016/0251376 A1 | 9/2016 | Dahlgren et al. | |
| 2018/0161329 A1 | 6/2018 | Mizuno et al. | |
| 2019/0076539 A1 | 3/2019 | Phillips et al. | |
| 2020/0216417 A1 | 7/2020 | Bernales et al. | |
| 2020/0331913 A1 | 10/2020 | Lindström et al. | |
| 2020/0392162 A1 | 12/2020 | Kesicki | |
| 2021/0253600 A1 | 8/2021 | Lindström et al. | |

FOREIGN PATENT DOCUMENTS

| | | |
|---|---|---|
| EP | 1165516 B1 | 10/2004 |
| EP | 1466906 A1 | 10/2004 |
| EP | 1690854 A1 | 8/2006 |
| EP | 3053577 A1 | 8/2016 |
| WO | WO-2000/055139 A2 | 9/2000 |
| WO | WO-2001/027103 A1 | 4/2001 |
| WO | WO-2002/083642 A1 | 10/2002 |
| WO | WO-2002/096876 A1 | 12/2002 |
| WO | WO-2003/022273 A1 | 3/2003 |
| WO | WO-2003/029210 A2 | 4/2003 |
| WO | WO-2003/062234 A1 | 7/2003 |
| WO | WO-2003/062236 A1 | 7/2003 |
| WO | WO-2003/068223 A1 | 8/2003 |

(Continued)

OTHER PUBLICATIONS

Golub et al., Science, vol. 286, Oct. 15, 1999, pp. 531-537. (Year: 1999).*
U.S. Appl. No. 18/303,264, filed Apr. 19, 2023, Aminopyridine Derivatives as Phosphatidylinositol Phosphate Kinase Inhibitors, Lindström et al.
Hinchliffe et al., "The type II PIPkins (ptdIns5p 4 kinases): enzymes in search of a function?", Biochem. Soc. Trans., 1999, vol. 27, No. 4, p. 657-661.
<http://butane.chem.uiuc.edu/jsmoore/chem232/notes_current/Stereochemistry/NOTES_current/Stereoisomers.pdf> Dec. 2009. (Year:2009).

(Continued)

*Primary Examiner* — Laura L Stockton
(74) *Attorney, Agent, or Firm* — Goodwin Procter LLP

(57) ABSTRACT

The invention relates to inhibitors of PI5P4K inhibitors useful in the treatment of cancers, neurodegenerative diseases, inflammatory disorders, and metabolic diseases, having the Formula:

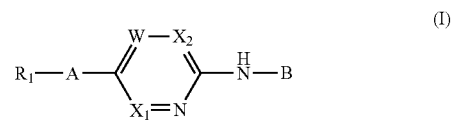

where A, B, $R_1$, $X_1$, $X_2$, and W are described herein.

15 Claims, No Drawings

(56) References Cited

FOREIGN PATENT DOCUMENTS

| WO | WO-2003/088897 A2 | 10/2003 | | |
|---|---|---|---|---|
| WO | WO-2004/030637 A2 | 4/2004 | | |
| WO | WO-2004/082586 A2 | 9/2004 | | |
| WO | WO-2005/018624 A2 | 3/2005 | | |
| WO | WO-2005/021529 A1 | 3/2005 | | |
| WO | WO-2005/023761 A2 | 3/2005 | | |
| WO | WO-2006/016680 A1 | 2/2006 | | |
| WO | WO-2007/030359 A1 | 3/2007 | | |
| WO | WO-2007/030366 A1 | 3/2007 | | |
| WO | WO-2007/056075 A2 | 5/2007 | | |
| WO | WO-2007/058990 A2 | 5/2007 | | |
| WO | WO-2007/071598 A1 | 6/2007 | | |
| WO | WO-2007/084786 A1 | 7/2007 | | |
| WO | WO-2007/091703 A1 | 8/2007 | | |
| WO | WO-2007/095588 A1 | 8/2007 | | |
| WO | WO-2007/110340 A2 | 10/2007 | | |
| WO | WO-2007/143456 A2 | 12/2007 | | |
| WO | WO-2007/146712 A2 | 12/2007 | | |
| WO | WO-2008/099000 A2 | 8/2008 | | |
| WO | WO-2008/138889 A2 | 11/2008 | | |
| WO | WO-2009/016118 A1 | 2/2009 | | |
| WO | WO-2009/044162 A1 | 4/2009 | | |
| WO | WO-2009/050227 A1 | 4/2009 | | |
| WO | WO-2009/085185 A1 | 7/2009 | | |
| WO | WO-2009/108838 A1 | 9/2009 | | |
| WO | WO-2009/156966 A1 | 12/2009 | | |
| WO | WO-2009/158431 A2 | 12/2009 | | |
| WO | WO-2010/014939 A1 | 2/2010 | | |
| WO | WO-2010/020675 A1 | 2/2010 | | |
| WO | WO-2010/027002 A1 | 3/2010 | | |
| WO | WO-2010/027002 A1 * | 3/2010 | ......... | A61K 31/5383 |
| WO | WO-2010/057833 A1 | 5/2010 | | |
| WO | WO-2010/075074 A1 | 7/2010 | | |
| WO | WO-2010/075282 A1 | 7/2010 | | |
| WO | WO-2010/100070 A1 | 9/2010 | | |
| WO | WO-2010/115264 A1 | 10/2010 | | |
| WO | WO-2010/139731 A1 | 12/2010 | | |
| WO | WO-2010/144345 A1 | 12/2010 | | |
| WO | WO-2011/021678 A1 | 2/2011 | | |
| WO | WO-2011/022473 A1 | 2/2011 | | |
| WO | WO-2011/031934 A1 | 3/2011 | | |
| WO | WO-2011/090738 A2 | 7/2011 | | |
| WO | WO-2011/101409 A1 | 8/2011 | | |
| WO | WO-2011/130232 A1 | 10/2011 | | |
| WO | WO-2012/035023 A1 | 3/2012 | | |
| WO | WO-2012/045124 A1 | 4/2012 | | |
| WO | WO-2012/095781 A1 | 7/2012 | | |
| WO | WO-2012/103806 A1 | 8/2012 | | |
| WO | WO-2012/158785 A1 | 11/2012 | | |
| WO | WO-2013/052394 A1 | 4/2013 | | |
| WO | WO-2013/106612 A1 | 7/2013 | | |
| WO | WO-2013/106614 A1 | 7/2013 | | |
| WO | WO-2013/106641 A1 | 7/2013 | | |
| WO | WO-2013/157540 A1 | 10/2013 | | |
| WO | WO-2013/192098 A1 | 12/2013 | | |
| WO | WO-2014/028459 A1 | 2/2014 | | |
| WO | WO-2014/060395 A1 | 4/2014 | | |
| WO | WO-2014/106800 A2 | 7/2014 | | |
| WO | WO-2014/110297 A1 | 7/2014 | | |
| WO | WO-2015/016206 A1 | 2/2015 | | |
| WO | WO-2015/098991 A1 | 7/2015 | | |
| WO | WO-2015/112441 A1 | 7/2015 | | |
| WO | WO-2015/131080 A1 | 9/2015 | | |
| WO | WO-2015/180642 A1 | 12/2015 | | |
| WO | WO-2016/015605 A1 | 2/2016 | | |
| WO | WO-2016/022644 A1 | 2/2016 | | |
| WO | WO-2016/027904 A1 | 2/2016 | | |
| WO | WO-2016/038583 A1 | 3/2016 | | |
| WO | WO-2016/070107 A1 | 5/2016 | | |
| WO | WO-2016/089208 A2 | 6/2016 | | |
| WO | WO-2016/128343 A1 | 8/2016 | | |
| WO | WO-2016/138352 A1 | 9/2016 | | |
| WO | WO-2016/166250 A1 | 10/2016 | | |
| WO | WO-2016/194831 A1 | 12/2016 | | |
| WO | WO-2016/210296 A1 | 12/2016 | | |
| WO | WO-2017/019804 A2 | 2/2017 | | |
| WO | WO-2017/071516 A1 | 5/2017 | | |
| WO | WO-2017/100726 A1 | 6/2017 | | |
| WO | WO-2017/101763 A1 | 6/2017 | | |
| WO | WO-2017/161045 A1 | 9/2017 | | |
| WO | WO-2017/185031 A1 | 10/2017 | | |
| WO | WO-2017/190086 A1 | 11/2017 | | |
| WO | WO-2017/197051 A1 | 11/2017 | | |
| WO | WO-2018/045956 A1 | 3/2018 | | |
| WO | WO-2018/045957 A1 | 3/2018 | | |
| WO | WO-2018/106870 A1 | 6/2018 | | |
| WO | WO-2018136202 A2 | 7/2018 | | |
| WO | WO-2018/177403 A1 | 10/2018 | | |
| WO | WO-2018/183112 A1 | 10/2018 | | |
| WO | WO-2018/232039 A1 | 12/2018 | | |
| WO | WO-2019/052535 A1 | 3/2019 | | |
| WO | WO-2019/079783 A1 | 4/2019 | | |
| WO | WO-2019/090198 A1 | 5/2019 | | |
| WO | WO-2019/126559 A1 | 6/2019 | | |
| WO | WO-2019/126731 A1 | 6/2019 | | |
| WO | WO-2019/152809 A1 | 8/2019 | | |
| WO | WO-2019/161224 A1 | 8/2019 | | |
| WO | WO-2019/191092 A1 | 10/2019 | | |
| WO | WO-2019/191229 A1 | 10/2019 | | |
| WO | WO-2019/213340 A1 | 11/2019 | | |
| WO | WO-2020/005873 A1 | 1/2020 | | |
| WO | WO-2020/023480 A1 | 1/2020 | | |
| WO | WO-2020/081450 A1 | 4/2020 | | |
| WO | WO-2020/097265 A1 | 5/2020 | | |
| WO | WO-2020/108661 A1 | 6/2020 | | |
| WO | WO-2020/109191 A1 | 6/2020 | | |
| WO | WO-2020/114487 A1 | 6/2020 | | |
| WO | WO-2020/114519 A1 | 6/2020 | | |
| WO | WO-2020/132700 A1 | 6/2020 | | |
| WO | WO-2020/142742 A1 | 7/2020 | | |
| WO | WO-2020/163409 A1 | 8/2020 | | |
| WO | WO-2020/163544 A1 | 8/2020 | | |
| WO | WO-2020/168197 A1 | 8/2020 | | |
| WO | WO-2020/207260 A1 | 10/2020 | | |
| WO | WO-2020/224568 A1 | 11/2020 | | |
| WO | WO-2020/231977 A1 | 11/2020 | | |
| WO | WO-2020/257271 A1 | 12/2020 | | |

OTHER PUBLICATIONS

Grant, R., Grant, C. (1987). Grant & Hackh's Chemical Dictionary (5th ed.). New York, NY: McGraw-Hill, p. 313.

Golub et al. "Molecular Classification of Cancer: Class Discovery and Class Prediction by Gene Expression Monitoring" Science, vol. 286, Oct. 15, 1999, pp. 531-537.

International Search Report and Written Opinion for PCT Application No. PCT/US2018/067264 dated Apr. 16, 2019.

van den Bout et al. "PIPSK-driven PtdIns(4,5) P2 synthesis: regulation and cellular functions" Journal of Cell Science 122, 3837-3850 Published by the Company of Biologists 2009.

CHEMCATS file; CAS Registry No. 2061527-02-2, STN entry date: Jan. 30, 2017; chemical name: 2-Pyrazinamine, 5-[1-(2-methyl-4-pyrimidinyl)-3-piperidinyl]-N-2-pyrazinyl-.

CHEMCATS file; CAS Registry No. 2060404-38-6, STN entry date: Jan. 27, 2017; chemical name: 2-Pyrazinamine, N-(6-methyl-2-pyridinyl)-5-[1-(4-pyrimidinyl)-3-piperidinyl]-.

CHEMCATS file: CAS Registry No. 2060404-08-0; STN entry date: Jan. 27, 2017; chemical name: 1-Piperidineacetamide, N,N-dimethyl-3-[5-(2-pyrazinylamino)-2-pyrazinyl]-.

CHEMCATS file: CAS Registry No. 1794062-09-1; STN entry date: Jul. 5, 2015; chemical name: 1-Piperidineacetamide, 2-[6-[(4,6-dimethyl-2-pyrimidinyl)amino]-3-pyridinyl]-N,N-dimethyl-.

CHEMCATS file: CAS Registry No. 1381025-64-4; STN entry date: Jul. 4, 2012; chemical name: 2-Pyrazinamine, 5-[1-(6-methyl-4-pyrimidinyl)-3-piperidinyl]-N-2-pyrazinyl-.

CHEMCATS file: CAS Registry No. 1381020-11-6; STN entry date: Jul. 4, 2012; chemical name: 2-Pyrimidinamine, N-[5-[1-(6-methyl-4-pyrimidinyl)-3-piperidinyl]-2-pyrazinyl]-.

CHEMCATS file: CAS Registry No. 1381019-89-1; STN entry date: Jul. 4, 2012; chemical name: 2-Pyrazinamine, N-2-pyrazinyl-5-[1-(2-pyrimidinyl)-3-piperidinyl]-.

(56) References Cited

OTHER PUBLICATIONS

CHEMCATS file: CAS Registry No. 1380993-08-7; STN entry date: Jul. 4, 2012; chemical name: 1-Piperidineacetamide, N,N-dimethyl-3-[5-[(6-methyl-2-pyridinyl)amino]-2-pyrazinyl]-.
CHEMCATS file: CAS Registry No. 1380992-98-2; STN entry date Jul. 4, 2012; chemical name: 1-Piperidineacetamide, N,N-dimethyl-3-[5-(2-pyridinylamino)-2-pyrazinyl]-.
CHEMCATS file: CAS Registry No. 1380898-52-1; STN entry date: Jul. 3, 2012; chemical name: 2-Pyrazinamine, 5-[1-(2-pyrimindinyl)-3-piperidinyl]-N-2-thiazolyl-.
CHEMCATS file: CAS Registry No. 1380855-52-6; STN entry date: Jul. 3, 2012; chemical name: 2-Pyrazinamine, N-2-pyridinyl-5-[1-(2-pyrimidinyl)-3-piperidinyl]-.
CHEMCATS file: CAS Registry No. 1380854-25-0; STN entry date: Jul. 3, 2012; chemical name: 2-Pyrazinamine, N-(6-methyl-2-pyridinyl)-5-[1-(2-pyrimidinyl)-3-piperidinyl]-.
CHEMCATS file: CAS Registry No. 1380852-13-0; STN entry date: Jul. 3, 2012; chemical name: 2-Pyrazinamine, 5-[1-(6-methyl-4-pyrimidinyl)-3-piperidinyl]-N-2-pyridinyl-.
Chemical Abstracts Registry No. 2133413-24-6, indexed in the Registry file on STN CAS Online on Oct. 9, 2017. (Year: 2017).
International Search Report and Written Opinion for PCT Application No. PCT/US2020/038121 dated Aug. 7, 2020.

\* cited by examiner

AMINOPYRIMIDINE DERIVATIVES AS PHOSPHATIDYLINOSITOL PHOSPHATE KINASE INHIBITORS

RELATED APPLICATIONS

This application is a continuation of U.S. patent application Ser. No. 16/904,073, filed on Jun. 17, 2020, which claims priority to, and the benefit of, U.S. Provisional Application No. 62/862,371, filed Jun. 17, 2019, the contents of each of which are incorporated by reference herein in their entirety for all purposes.

FIELD OF INVENTION

The present invention is directed to inhibitors of phosphatidylinositol-5-phosphate-4-kinase (PI5P4K) useful in the treatment of diseases or disorders associated with PI5P4K enzymes. In particular, the invention is concerned with compounds and compositions inhibiting PI5P4K, methods of treating diseases or disorders associated with PI5P4K, and methods of synthesis of these compounds.

BACKGROUND OF THE INVENTION

A minor but ubiquitous component of cells, phosphoinositol lipids are pivotal players in many intracellular signal transduction pathways. Phosphoinositol lipids are formed when phosphatidylinositol (PtdIns) is converted, by the catalytic action of lipid kinases, to polyphosphoinositides. As a prototypic example, the membrane associated phospholipid, phosphatidylinositol-4,5-bisphosphate (PtdIns(4, 5)P2), is formed by two successive phosphorylations of PtdIns by the phosphatidylinositol phosphate kinases (PIP kinases).

PtdIns(4,5)P2 is a substrate for phospholipase C (PLC) and is converted into the second messengers inositol-1,4,5-trisphosphate and diacylglycerol (DAG). Phosphoinositides are involved in regulating a broad spectrum of activities from cytoskeletal assembly and motility to vesicle trafficking and exocytosis to transduction of intracellular signals including stimulating the release of intracellular calcium stores (Hinchliffe et al., *Biochem. Soc. Trans.*, 1999, 27, 657-661).

PIP kinases comprise a unique and promiscuous family of enzymes that catalyze the production of poly-phosphorylated inositol lipids from mono-phosphorylated phosphoinositides. isolation and purification of several different PIP kinase enzymes able to catalyze phosphorylation of phosphatidylinositol 4-phosphate and produce PtdIns(4,5)P2 led to the further categorization of these enzymes, dubbed the phosphatidylinositol 4-phosphate 5-kinases (PIP5Ks), into two types having different activities. The PIP kinases have no homology to other lipid or protein kinases at the primary sequence level, and are distinguished from each other by their lack of immuno-cross reactivity and by the fact that type I PIP5Ks are stimulated in vitro by phosphatidic acid, whereas the type II PIP5Ks are not. Furthermore, the recent discovery that the type II PTP5Ks are able to phosphorylate multiple lipid substrates in vitro suggests that this family of kinases is potentially able to generate several distinct, often subcellularly compartmentalized, phosphoinositol products for regulation of a variety of physiologically important processes (Hinchliffe et al., *Biochem. Soc. Trans.*, 1999, 27, 657-661).

One particular species of PI, phosphatidylinositol 5-phosphate (PI5P), has been implicated in the regulation of the tumor suppressor ING2 and the oncogene AKT. The phosphatidylinositol 5-phosphate 4-kinase (PI5P4K) family (α, β, γ isoforms) catalyzes the conversion of PI5P to PI4, 5 P2. These enzymes therefore represent one means by which cells can regulate endogenous PI5P levels. Mice deficient for PI5P4Kβ (PI5P4Kβ−/−) have been shown to exhibit enhanced insulin sensitivity and activation of AKT in skeletal muscle.

The pharmacological modulation of PIP5KII-beta activity and/or expression is therefore believed to be an appropriate point of therapeutic intervention in pathological conditions in which cell differentiation, proliferation, and/or motility are compromised, such as cancer or inflammation, and in metabolic disorders.

Currently, there are no known therapeutic agents which effectively inhibit the synthesis of PIP5KII-beta. Inhibition of PI5P4K with small molecule inhibitors, therefore, has the potential to be a treatment for cancers and other disorders. For this reason, there remains a considerable need for novel and potent small molecule inhibitors and agents capable of effectively inhibiting PIP5KII-beta function.

SUMMARY OF THE INVENTION

A first aspect of the invention relates to compounds of Formula (I):

$$R_1-A-\underset{X_1=N}{\overset{W-X_2}{\diagdown}}-\overset{H}{N}-B \qquad (I)$$

or a pharmaceutically acceptable salt, prodrug, solvate, hydrate, isomer, or tautomer thereof, wherein:

A is aryl;

B is heteroaryl, substituted with one or more $R_8$, provided that when B is heteroaryl, B is not bonded through its heteroatom;

$X_1$ is $C(R_5)$;

$X_2$ is $C(R_5)$ or N;

W is $C(R_6)$;

$R_1$ is $-N(R_2)C(O)R_3$, $-C(O)N(R_2)(R_3)$, $-P(O)(R_2)(R_3)$, or heteroaryl, wherein the heteroaryl is optionally substituted with one or more $R_7$;

$R_2$ is independently, at each occurrence, $C_{1-6}$ alkyl;

$R_3$ is independently, at each occurrence, $C_{1-6}$ alkyl or $C_3$-s cycloalkyl; or $R_2$ and $R_3$ when taken together with the atom to which they are each attached form a heterocycle optionally substituted with one or more $R_4$;

$R_4$ is independently —H or $C_{1-6}$ alkyl;

$R_5$ is independently —H;

$R_6$ is —H, —N($R_{26}$)($R_{27}$), $C_{1-6}$ alkoxy, heterocyclyl, $C_{1-6}$ alkenyl, $C_{1-6}$ haloalkyl, or $C_{1-6}$ alkyl, wherein the alkyl, alkenyl, alkoxy, or heterocyclyl, is optionally substituted with one or more —OH, —CN, $C_{1-6}$ alkyl, or heterocyclyl;

$R_7$ is $C_{1-6}$ alkyl;

$R_8$ is heterocyclyl, —N($R_9$)($R_{10}$), or —O$R_{10}$, wherein the heterocyclyl is optionally substituted with one or more $R_{15}$; or two $R_8$ groups, together with the atoms to which they are attached, form a heterocyclyl, optionally substituted with one or more $R_{15}$;

each $R_9$ or $R_{10}$ is independently, at each occurrence, $C_{1-6}$ alkyl optionally substituted with one or more $R_{11}$;

$R_{11}$ is —OH, heterocyclyl, —C(O)$R_{17}$, or —C(O)N($R_{23}$)($R_{23}$), wherein the heterocyclyl is optionally substituted with one or more $R_{17}$;

$R_{15}$ is —N($C_{1-6}$ alkyl)$_2$, $C_{1-6}$ alkyl, —C(O)N($R_{21}$)($R_{23}$), —(CH$_2$)$_o$—C(O)$R_{23}$, or —C(O)O$R_{23}$, wherein the alkyl, is optionally substituted with one or more $R_{23}$; or two $R_{15}$ groups, together with the atoms to which they are attached, form a heterocyclyl optionally substituted with one or more $R_{20}$;

$R_{17}$ is halogen or $C_{1-6}$ alkyl;

$R_{20}$ is independently oxo or $C_{1-6}$ alkyl, wherein the $C_{1-6}$ alkyl is substituted with heterocyclyl;

$R_{21}$ is —H or $C_{1-6}$ alkyl;

each $R_{23}$ is independently $C_{1-6}$ alkyl, optionally substituted with one or more —N($C_{1-6}$ alkyl)$_2$; or two $R_{23}$ together form a heterocyclyl, wherein the heterocyclyl is optionally substituted by $C_{1-6}$ alkyl;

$R_{26}$ is —H or $C_{1-6}$ alkyl;

$R_{27}$ is $C_{1-6}$ alkyl, heterocyclyl, or cycloalkyl, wherein the alkyl, heterocyclyl, or cycloalkyl is optionally substituted with one or more halogen, —CN, —C(O)OH, —OH, or —NH$_2$; and each o is independently 0-4, provided that $R_8$ is not methoxy.

Another aspect of the invention relates to a method of treating a disease or disorder associated with modulation of PI5P4K. The method comprises administering to a patient in need of a treatment for diseases or disorders associated with modulation of PI5P4K an effective amount of a compound of Formula (I), or a pharmaceutically acceptable salt, hydrate, solvate, prodrug, stereoisomer, or tautomer thereof.

Another aspect of the invention is directed to a method of inhibiting PI5P4K. The method involves administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a neurodegenerative disease. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a viral infection or disease. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating an inflammatory disease or condition. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of inducing cell cycle arrest, apoptosis in tumor cells and/or enhanced tumor-specific T-cell immunity. The method comprises contacting the cells with an effective amount of a compound of Formula (I), or a pharmaceutically acceptable salt, hydrate, solvate, prodrug, stereoisomer, or tautomer thereof.

Another aspect of the invention is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with inhibiting PI5P4K.

Another aspect of the present invention relates to the use of a compound of Formula (I), or a pharmaceutically acceptable salt, hydrate, solvate, prodrug, stereoisomer, or tautomer thereof, in the treatment of a disease associated with inhibiting PI5P4K.

The present invention further provides methods of treating a disease or disorder associated with modulation of PI5P4K including, cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases, comprising administering to a patient suffering from at least one of said diseases or disorder a compound of Formula (I), or a pharmaceutically acceptable salt, hydrate, solvate, prodrug, stereoisomer, or tautomer thereof.

The present invention provides inhibitors of PI5P4K that are therapeutic agents in the treatment of diseases such as cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

The present invention further provides compounds and compositions with an improved efficacy and safety profile relative to known PI5P4K inhibitors. The present disclosure also provides agents with novel mechanisms of action toward PI5P4K enzymes in the treatment of various types of diseases including cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases. Ultimately the present invention provides the medical community with a novel pharmacological strategy for the treatment of diseases and disorders associated with PI5P4K enzymes.

DETAILED DESCRIPTION OF THE INVENTION

The present invention relates to compounds and compositions that are capable of inhibiting the activity PI5P4K. The invention features methods of treating, preventing or ameliorating a disease or disorder in which PI5P4K plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of PI5P4K dependent diseases and disorders by inhibiting the activity of PI5P4K enzymes. Inhibition of PI5P4K provides a novel approach to the treatment, prevention, or amelioration of diseases including, but not limited to, cancer and metastasis, neurodegenerative diseases, immunological disorders, osteoporosis, arthritis inflammatory disorders, cardiovascular diseases, ischemic diseases, viral infections and diseases, and bacterial infections and diseases.

In a first aspect of the invention, the compounds of Formula (I) are described:

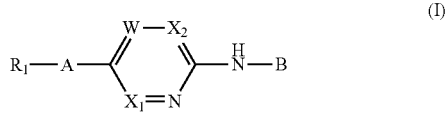

(I)

and pharmaceutically acceptable salts, hydrates, solvates, prodrugs, stereoisomers, and tautomers thereof, wherein A, B, $R_1$, $X_1$, $X_2$, and W are described herein above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have one or more substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O ($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$)alkyl, and —S(O) N(($C_1$-$C_6$)alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$)alkyl, ($C_1$-$C_6$)alkyl, —O—($C_2$-$C_6$)alkenyl, —O—($C_2$-$C_6$) alkynyl, ($C_2$-$C_6$)alkenyl, ($C_2$-$C_6$)alkynyl, —OH, —OP(O)(OH)$_2$, —OC(O)($C_1$-$C_6$) alkyl, —C(O)($C_1$-$C_6$) alkyl, —OC(O)O($C_1$-$C_6$)alkyl, —NH$_2$, —NH(($C_1$-$C_6$)alkyl), —N(($C_1$-$C_6$)alkyl)$_2$, —S(O)$_2$—($C_1$-$C_6$) alkyl, —S(O)NH($C_1$-$C_6$)alkyl, and —S(O)N(($C_1$-$C_6$)alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or a polycyclic aromatic radical of 5 to 24 ring atoms, containing one or more ring heteroatoms selected from N, O, S, P, or B, the remaining ring atoms being C. A polycyclic aromatic radical includes two or more fused rings and may further include two or more spiro-fused rings, e.g., bicyclic, tricyclic, tetracyclic, and the like. Unless otherwise specifically defined, "fused" means two rings sharing two ring atoms. Unless otherwise specifically defined, "spiro-fused" means two rings sharing one ring atom. Heteroaryl as herein defined also means a bicyclic heteroaromatic group wherein the heteroatom is selected from N, O, S, P, or B. Heteroaryl as herein defined also means a tricyclic heteroaromatic group containing one or more ring heteroatoms selected from N, O, S, P, or B. Heteroaryl as herein defined also means a tetracyclic heteroaromatic group containing one or more ring heteroatoms selected from N, O, S, P, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2, 3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1-pyrrolo[2,1-b]pyrimidine, dibenzo[b,d] thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with one or more fully unsaturated ring. In heteroaryl ring systems containing more than two fused rings, a saturated or partially unsaturated ring may further be fused with a saturated or partially unsaturated ring described herein. Furthermore, when containing three or more fused rings, the heteroaryl groups defined herein may have one or more saturated or partially unsaturated ring spiro-fused. Any saturated or partially unsaturated ring described herein is optionally substituted with one or more oxo. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7(4H)-only, 3,4-dihydropyrazino[1,2-a]indol-1(2H)-onyl, benzo[c][1,2]oxaborol-1(3H)-olyl, 6,6a,7,8-tetrahydro-9H-pyrido[2,3-b]puyrrolo[1,2-d][1,4]oxazin-9-onyl, or 6',7'-dihydro-6'H,9'H-spiro[cyclopropane-1,8'-pyrido[2,3-b]pyrrolo[1,2-d][1,4]oxazin]-9'-onyl.

Halogen or "halo" refers to fluorine, chlorine, bromine, or iodine.

Alkyl refers to a straight or branched chain saturated hydrocarbon containing 1-12 carbon atoms. Examples of a $(C_1-C_6)$ alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1-C_6$ alkylene. An alkylene may further be a $C_1-C_4$ alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norbornyl, norborenyl, bicyclo[2.2.2]octanyl, or bicyclo[2.2.2]octenyl.

"Cycloalkylalkyl" means monocyclic saturated carbon rings containing 3-24 carbon atoms further substituted with $(C_1-C_6)$ alkyl groups. In general cycloalkylalkyl groups herein described display the following formula

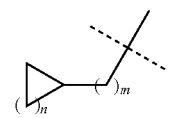

where m is an integer from 1 to 6 and n is an integer from 1 to 16. The cycloalkyl ring or carbocycle may be optionally substituted by one or more substituents, e.g., 1 to 5 substituents, at any point of attachment. The substituents can themselves be optionally substituted. Examples of cycloalkyl groups include, without limitations, cyclopropyl, cyclobutyl, cyclopentyl, cyclohexyl, cycloheptanyl, cyclooctanyl, norbornyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, and derivatives thereof.

"Heterocyclyl" or "heterocycloalkyl" monocyclic rings contain carbon and one or more heteroatoms selected from N, O, S, P, or B and wherein the rings are not aromatic. The heterocycloalkyl ring structure may be substituted by one or more substituents. The substituents can themselves be optionally substituted. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "aromatic" means a planar ring having 4n+2 electrons in a conjugated system. As used herein, "conjugated system" means a system of connected p-orbitals with delocalized electrons, and the system may include lone electron pairs.

The term "hydroxyalkyl" means an alkyl group as defined above, where the alkyl group is substituted with one or more OH groups. Examples of hydroxyalkyl groups include HO—$CH_2$—, HO—$CH_2$—$CH_2$— and $CH_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary ($R$—$NH_2$, R≠H), secondary ($R_2$—NH, $R_2$ #H) and tertiary ($R_3$—N, R #H) amines. A substituted amine is intended to mean an amine where at least one of the hydrogen atoms has been replaced by the substituent.

The term "amino" as used herein means a substituent containing at least one nitrogen atom. Specifically, —$NH_2$, —NH(alkyl) or alkylamino, —N(alkyl)$_2$ or dialkylamino, amide-, carbamide-, urea, and sulfamide substituents are included in the term "amino".

The term "dialkylamino" as used herein refers to an amino or —$NH_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethylamino (i.e., —N($CH_3$)$_2$), diethylamino, dipropylamino, diisopropylamino, di-n-butylamino, di-sec-butylamino, di-tert-butylamino, methyl(ethyl)amino, methyl(butylamino), etc.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A ($C_3$-$C_{12}$) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperidinyl).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically-labelled compounds of Formula I (e.g., those labeled with $^2$H and $^{14}$C). Deuterated (i.e., $^2$H or D) and carbon-14 (i.e., $^{14}$C) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, pantothenate, phosphate/diphosphate, picrate, polygalacturonate, propionate, p-toluenesulfonate, salicylate, stearate, subacetate, succinate, sulfate, sulfosalicylate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting PI5P4K, which are useful for the treatment of diseases and disorders associated with modulation of a PI5P4K enzyme. The invention further relates to compounds, or pharmaceutically acceptable salts, hydrates, solvates, prodrugs, stereoisomers, or tautomers thereof, which are useful for inhibiting PI5P4K.

In another embodiment, the compounds of Formula (I) have the structure of Formula (Ia):

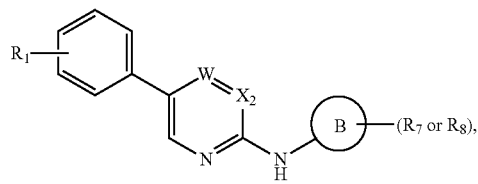

(Ia)

wherein $X_2$ is $C(R_5)$ or N and W is $C(R_6)$.

In another embodiment, the compounds of Formula (I) have the structure of Formula (Ib):

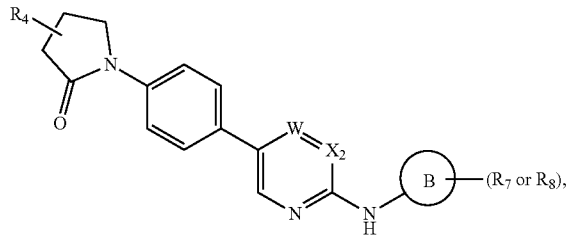

(Ib)

wherein $X_2$ is $C(R_5)$ or N and W is $C(R_6)$.

In another embodiment, the compounds of Formula (I) have the structure of Formula (Ic):

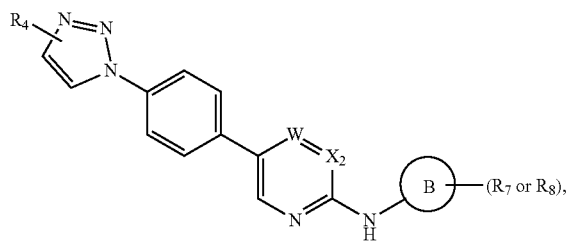

(Ic)

wherein $X_2$ is $C(R_5)$ or N and W is $C(R_6)$.

In another embodiment, the compounds of Formula (I) have the structure of Formula (Id):

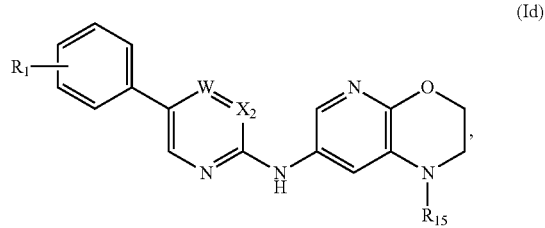

(Id)

wherein $X_2$ is $C(R_5)$ or N and W is $C(R_6)$.

In another embodiment, the compounds of Formula (I) have the structure of Formula (Ie):

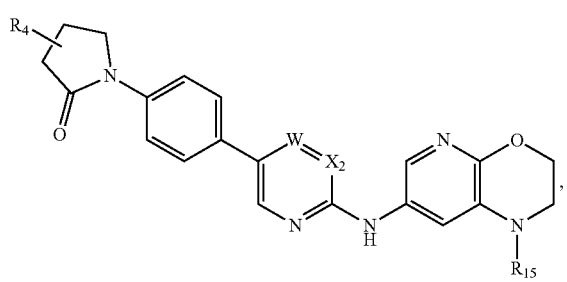

(Ie)

wherein $X_2$ is $C(R_5)$ or N and W is $C(R_6)$.

In another embodiment, the compounds of Formula (I) have the structure of Formula (If):

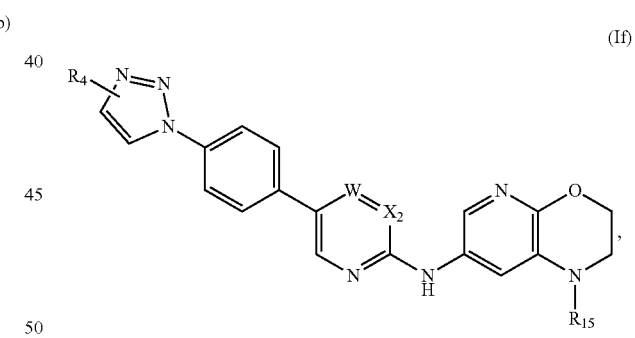

(If)

wherein $X_2$ is $C(R_5)$ or N and W is $C(R_6)$.

In some embodiments of the compounds of Formula I, $R_1$ is —$N(R_2)C(O)R_3$, —$C(O)N(R_2)(R_3)$, —$P(O)(R_2)(R_3)$, or heteroaryl, wherein heteroaryl is optionally substituted with $R_7$. In another embodiment $R_1$ is —$N(R_2)C(O)R_3$, —$C(O)N(R_2)(R_3)$, —$P(O)(R_2)(R_3)$, or heteroaryl. In another embodiment, $R_1$ is —$N(R_2)C(O)R_3$, —$C(O)N(R_2)(R_3)$, —$P(O)(R_2)(R_3)$. In another embodiment, $R_1$ is —$N(R_2)C(O)R_3$. In another embodiment, $R_1$ is —$C(O)N(R_2)(R_3)$. In another embodiment, $R_1$ is —$P(O)(R_2)(R_3)$. In another embodiment, $R_1$ is heteroaryl. In another embodiment, $R_1$ is heteroaryl, wherein heteroaryl is optionally substituted with $R_7$.

In some embodiments of the compounds of Formula I, W is $C(R_6)$.

In some embodiments of the compounds of Formula I, A is aryl.

In some embodiments of the compounds of Formula I, B is heteroaryl. In one embodiment, B is heteroaryl optionally substituted with one or two $R_8$. In one embodiment, B is heteroaryl optionally substituted with one or two $R_8$, wherein B is not bonded through its heteroatom In some embodiments of the compounds of Formula I, $X_1$ is $C(R_5)$.

In some embodiments of the compounds of Formula I, $X_2$ is $C(R_5)$ or N. In one embodiment, $X_2$ is $C(R_5)$. In one embodiment, $X_2$ is N.

In some embodiments of the compounds of Formula I, $R_2$ is $C_{1-6}$ alkyl. In some embodiments of the compounds of Formula I, $R_2$ is $C_{1-5}$ alkyl. In some embodiments of the compounds of Formula I, $R_2$ is $C_{1-4}$ alkyl. In some embodiments of the compounds of Formula I, $R_2$ is $C_{2-6}$ alkyl. In some embodiments of the compounds of Formula I, $R_2$ is $C_1$ alkyl. In some embodiments of the compounds of Formula I, $R_2$ is $C_2$ alkyl. In some embodiments of the compounds of Formula I, $R_2$ is $C_3$ alkyl. In some embodiments of the compounds of Formula I, $R_2$ is $C_4$ alkyl. In some embodiments of the compounds of Formula I, $R_2$ is $C_5$ alkyl. In some embodiments of the compounds of Formula I, $R_2$ is $C_6$ alkyl.

In some embodiments of the compounds of Formula I, $R_3$ is $C_{1-6}$ alkyl or $C_{3-8}$ cycloalkyl. In another embodiment, $R_3$ is $C_{1-6}$ alkyl. In some embodiments of the compounds of Formula I, $R_3$ is $C_{1-5}$ alkyl. In some embodiments of the compounds of Formula I, $R_3$ is $C_{1-4}$ alkyl. In some embodiments of the compounds of Formula I, $R_3$ is $C_{2-6}$ alkyl. In some embodiments of the compounds of Formula I, $R_3$ is $C_1$ alkyl. In some embodiments of the compounds of Formula I, $R_3$ is $C_2$ alkyl. In some embodiments of the compounds of Formula I, $R_3$ is $C_3$ alkyl. In some embodiments of the compounds of Formula I, $R_3$ is $C_4$ alkyl. In some embodiments of the compounds of Formula I, $R_3$ is $C_5$ alkyl. In some embodiments of the compounds of Formula I, $R_3$ is $C_6$ alkyl. In another embodiment, $R_3$ is $C_{3-8}$ cycloalkyl.

In other embodiments of the compounds of Formula I, $R_2$ and $R_3$ when taken together with the atom to which they are attached form a heterocycle. In another embodiment, $R_2$ and $R_3$ when taken together with the atom to which they are attached form a heterocycle optionally substituted with one or more $R_4$.

In other embodiments of the compounds of Formula I, $R_4$ is —H, or $C_{1-6}$ alkyl. In another embodiment, $R_4$ is —H. In another embodiment, $R_4$ is $C_{1-6}$ alkyl. In some embodiments of the compounds of Formula I, $R_4$ is $C_{1-5}$ alkyl. In some embodiments of the compounds of Formula I, $R_4$ is $C_{1-4}$ alkyl. In some embodiments of the compounds of Formula I, $R_4$ is $C_{2-6}$ alkyl. In some embodiments of the compounds of Formula I, $R_4$ is $C_1$ alkyl. In some embodiments of the compounds of Formula I, $R_4$ is $C_2$ alkyl. In some embodiments of the compounds of Formula I, $R_4$ is $C_3$ alkyl. In some embodiments of the compounds of Formula I, $R_4$ is $C_4$ alkyl. In some embodiments of the compounds of Formula I, $R_4$ is $C_5$ alkyl. In some embodiments of the compounds of Formula I, $R_4$ is $C_6$ alkyl.

In other embodiments of the compounds of Formula I, $R_5$ is —H.

In other embodiments of the compounds of Formula I, $R_6$ is —H, —N($R_{26}$)($R_{27}$), $C_{1-6}$ alkoxy, heterocyclyl, $C_{1-6}$ alkenyl, $C_{1-6}$ haloalkyl, or $C_{1-6}$ alkyl. In other embodiments of the compounds of Formula I, $R_6$ is —N($R_{26}$)($R_{27}$), $C_{1-6}$ alkoxy, heterocyclyl, $C_{1-6}$ alkenyl, $C_{1-6}$ haloalkyl, or $C_{1-6}$ alkyl. In other embodiments of the compounds of Formula I, $R_6$ is —N($R_{26}$)($R_{27}$), $C_{1-6}$ alkoxy, $C_{1-6}$ alkenyl, $C_{1-6}$ haloalkyl, or $C_{1-6}$ alkyl. In other embodiments of the compounds of Formula I, $R_6$ is —N($R_{26}$)($R_{27}$), $C_{1-6}$ alkoxy, $C_{1-6}$ alkenyl, or $C_{1-6}$ alkyl. In other embodiments of the compounds of Formula I, $R_6$ is —N($R_{26}$)($R_{27}$), $C_{1-6}$ alkoxy, or $C_{1-6}$ alkyl. In other embodiments of the compounds of Formula I, $R_6$ is —N($R_{26}$)($R_{27}$) or $C_{1-6}$ alkyl. In other embodiments of the compounds of Formula I, $R_6$ is —H, —N($R_{26}$)($R_{27}$), $C_{1-6}$ alkoxy, heterocyclyl, $C_{1-6}$ alkenyl, $C_{1-6}$ haloalkyl, or $C_{1-6}$ alkyl, wherein the alkyl, alkoxy, or heterocyclyl, is optionally substituted with —OH, —CN, C1-6 alkyl, or heterocyclyl. In another embodiment, $R_6$ is H. In another embodiment, $R_6$ is —N($R_{26}$)($R_{27}$). In another embodiment, $R_6$ is $C_{1-6}$ alkoxy. In another embodiment, $R_6$ is heterocyclyl. In another embodiment, $R_6$ is $C_{1-6}$ alkenyl. In another embodiment, $R_6$ is $C_{1-6}$ haloalkyl. In another embodiment, $R_6$ is $C_{1-6}$ alkyl. In another embodiment, $R_6$ is $C_{1-6}$ alkoxy optionally substituted with —OH, —CN, $C_{1-6}$ alkyl, or heterocyclyl. In another embodiment, $R_6$ is heterocyclyl optionally substituted with —OH, —CN, $C_{1-6}$ alkyl, or heterocyclyl. In another embodiment, $R_6$ is $C_{1-6}$ alkenyl optionally substituted with —OH, —CN, $C_{1-6}$ alkyl, or heterocyclyl. In another embodiment, $R_6$ is $C_{1-6}$ haloalkyl optionally substituted with —OH, —CN, $C_{1-6}$ alkyl, or heterocyclyl. In another embodiment, $R_6$ is $C_{1-6}$ alkyl optionally substituted with —OH, —CN, $C_{1-6}$ alkyl, or heterocyclyl.

In other embodiments of the compounds of Formula I, $R_7$ is $C_{1-6}$ alkyl. In some embodiments of the compounds of Formula I, $R_7$ is $C_{1-5}$ alkyl. In some embodiments of the compounds of Formula I, $R_7$ is $C_{1-4}$ alkyl. In some embodiments of the compounds of Formula I, $R_7$ is $C_{2-6}$ alkyl. In some embodiments of the compounds of Formula I, $R_7$ is $C_1$ alkyl. In some embodiments of the compounds of Formula I, $R_7$ is $C_2$ alkyl. In some embodiments of the compounds of Formula I, $R_7$ is $C_3$ alkyl. In some embodiments of the compounds of Formula I, $R_7$ is $C_4$ alkyl. In some embodiments of the compounds of Formula I, $R_7$ is $C_5$ alkyl. In some embodiments of the compounds of Formula I, $R_7$ is $C_6$ alkyl.

In other embodiments of the compounds of Formula I, $R_8$ is heterocyclyl, —N($R_9$)($R_{10}$), or —$OR_{10}$. In other embodiments of the compounds of Formula I, $R_8$ is heterocyclyl, —N($R_9$)($R_{10}$), or —$OR_{10}$, wherein the heterocyclyl, is optionally substituted with one or more $R_{15}$. In another embodiment, $R_8$ is heterocyclyl. In another embodiment, $R_8$ is heterocyclyl optionally substituted with one or more $R_{15}$. In another embodiment, $R_8$ is —N($R_9$)($R_{10}$). In another embodiment, $R_8$ is —$OR_{10}$.

In other embodiments of the compounds of Formula I, two $R_8$ groups together with the atoms to which they are attached, form a heterocyclyl. In some embodiments, $R_8$ groups, together with the atoms to which they are attached, form a heterocyclyl optionally substituted with one or more $R_{15}$.

In some embodiments of the compounds of Formula I, $R_9$ is $C_{1-6}$ alkyl. In another embodiment, $R_9$ is $C_{1-6}$ alkyl optionally substituted with one or more $R_{11}$. In some embodiments of the compounds of Formula I, $R_9$ is $C_{1-5}$ alkyl. In some embodiments of the compounds of Formula I, $R_9$ is $C_{1-4}$ alkyl. In some embodiments of the compounds of Formula I, $R_9$ is $C_{2-6}$ alkyl. In some embodiments of the compounds of Formula I, $R_9$ is $C_1$ alkyl. In some embodiments of the compounds of Formula I, $R_9$ is $C_2$ alkyl. In some embodiments of the compounds of Formula I, $R_9$ is $C_3$ alkyl. In some embodiments of the compounds of Formula I, $R_9$ is $C_4$ alkyl. In some embodiments of the compounds of Formula I, $R_9$ is $C_5$ alkyl. In some embodiments of the compounds of Formula I, $R_9$ is $C_6$ alkyl. In some embodiments of the compounds of Formula I, $R_9$ is $C_{1-5}$ alkyl optionally substituted with one or more $R_{11}$. In some embodiments of the compounds of Formula I, $R_9$ is $C_{1-4}$ alkyl optionally substituted with one or more $R_{11}$. In some embodiments of the compounds of Formula I, $R_9$ is $C_{2-6}$ alkyl optionally substituted with one or more $R_{11}$. In some embodiments of the compounds of Formula I, $R_9$ is $C_1$ alkyl optionally substituted with one or more $R_{11}$. In some embodiments of the compounds of Formula I, $R_9$ is $C_2$ alkyl optionally substituted with one or more $R_{11}$. In some embodiments of the compounds of Formula I, $R_9$ is $C_3$ alkyl optionally substituted with one or more $R_{11}$. In some embodiments of the compounds of Formula I, $R_9$ is $C_4$ alkyl optionally substituted with one or more $R_{11}$. In some embodiments of the compounds of Formula I, $R_9$ is $C_5$ alkyl optionally substituted with one or more $R_{11}$. In some embodiments of the compounds of Formula I, $R_9$ is $C_6$ alkyl optionally substituted with one or more $R_{11}$.

In some embodiments of the compounds of Formula I, $R_{10}$ is $C_{1-6}$ alkyl. In another embodiment, $R_{10}$ is $C_{1-6}$ alkyl optionally substituted with one or more $R_{11}$. In some embodiments of the compounds of Formula I, $R_{10}$ is $C_{1-5}$ alkyl. In some embodiments of the compounds of Formula I, $R_{10}$ is $C_{1-4}$ alkyl. In some embodiments of the compounds of Formula I, $R_{10}$ is $C_{2-6}$ alkyl. In some embodiments of the compounds of Formula I, $R_{10}$ is $C_1$ alkyl. In some embodiments of the compounds of Formula I, $R_{10}$ is $C_2$ alkyl. In some embodiments of the compounds of Formula I, $R_{10}$ is $C_3$ alkyl. In some embodiments of the compounds of Formula I, $R_{10}$ is $C_4$ alkyl. In some embodiments of the compounds of Formula I, $R_{10}$ is $C_5$ alkyl. In some embodiments of the compounds of Formula I, $R_{10}$ is $C_6$ alkyl. In some embodiments of the compounds of Formula I, $R_{10}$ is $C_{1-5}$ alkyl optionally substituted with one or more $R_{11}$. In some embodiments of the compounds of Formula I, $R_{10}$ is $C_{1-4}$ alkyl optionally substituted with one or more $R_{11}$. In some embodiments of the compounds of Formula I, $R_{10}$ is $C_{2-6}$ alkyl optionally substituted with one or more $R_{11}$. In some embodiments of the compounds of Formula I, $R_{10}$ is $C_1$ alkyl optionally substituted with one or more $R_{11}$. In some embodiments of the compounds of Formula I, $R_{10}$ is $C_2$ alkyl optionally substituted with one or more $R_{11}$. In some embodiments of the compounds of Formula I, $R_{10}$ is $C_3$ alkyl optionally substituted with one or more $R_{11}$. In some embodiments of the compounds of Formula I, $R_{10}$ is $C_4$ alkyl optionally substituted with one or more $R_{11}$. In some embodiments of the compounds of Formula I, $R_{10}$ is $C_5$ alkyl optionally substituted with one or more $R_{11}$. In some embodiments of the compounds of Formula I, $R_{10}$ is $C_6$ alkyl optionally substituted with one or more $R_{11}$.

In other embodiments of the compounds of Formula I, $R_{11}$ is —OH, heterocyclyl, —C(O)$R_{17}$, or —C(O)N($R_{23}$)($R_{23}$). In another embodiment, $R_{11}$ is —OH. In another embodiment, $R_{11}$ is heterocyclyl. In another embodiment, $R_{11}$ is —C(O)$R_{17}$. In another embodiment, $R_{11}$ is —C(O)N($R_{23}$)($R_{23}$). In another embodiment, $R_{11}$ is heterocyclyl optionally substituted with one or more $R_{17}$.

In some embodiments of the compounds of Formula I, $R_{15}$ is —N($C_{1-6}$ alkyl)$_2$, $C_{1-6}$ alkyl, —C(O)N($R_{21}$)($R_{23}$), —(CH$_2$)$_o$—C(O)$R_{23}$, or —C(O)O$R_{23}$. In some embodiments of the compounds of Formula I, $R_{15}$ is —N($C_{1-6}$ alkyl)$_2$, $C_{1-6}$ alkyl, —C(O)N($R_{21}$)($R_{23}$), —(CH$_2$)$_o$—C(O)$R_{23}$, or —C(O)O$R_{23}$, wherein the alkyl, is optionally substituted with one or more $R_{23}$. In some embodiments of the compounds of Formula I, $R_{15}$ is —N($C_{1-6}$ alkyl)$_2$. In some embodiments of the compounds of Formula I, $R_{15}$ is $C_{1-6}$ alkyl. In some embodiments of the compounds of Formula I, $R_{15}$ is $C_{1-6}$ alkyl optionally substituted with one or more $R_{23}$. In some embodiments of the compounds of Formula I, $R_{15}$ is —C(O)N($R_{21}$)($R_{23}$). In some embodiments of the compounds of Formula I, $R_{15}$ is —(CH$_2$)$_o$—C(O)$R_{23}$. In some embodiments of the compounds of Formula I, $R_{15}$ is —C(O)O$R_{23}$.

In other embodiments of the compounds of Formula I, two $R_{15}$ groups, together with the atoms to which they are attached, form a heterocyclyl. In another embodiment, two $R_{15}$ when on adjacent atoms may be taken together with the atoms to which they are each attached to form a heterocyclyl substituted with one or more $R_{20}$.

In some embodiments of the compounds of Formula I, $R_{17}$ is halogen or —$C_{1-6}$ alkyl. In some embodiments of the compounds of Formula I, $R_{17}$ is halogen. In some embodiments of the compounds of Formula I, $R_{17}$ is F, Cl, Br, or I. In some embodiments of the compounds of Formula I, $R_{17}$ is F or Cl. In some embodiments of the compounds of Formula I, $R_{17}$ is F. In some embodiments of the compounds of Formula I, $R_{17}$ is Cl. In some embodiments of the compounds of Formula I, $R_{17}$ is —$C_{1-6}$ alkyl. In some embodiments of the compounds of Formula I, $R_{17}$ is $C_{1-5}$ alkyl. In some embodiments of the compounds of Formula I, $R_{17}$ is $C_{1-4}$ alkyl. In some embodiments of the compounds of Formula I, $R_{17}$ is $C_{2-6}$ alkyl. In some embodiments of the compounds of Formula I, $R_{17}$ is $C_1$ alkyl. In some embodiments of the compounds of Formula I, $R_{17}$ is $C_2$ alkyl. In some embodiments of the compounds of Formula I, $R_{17}$ is $C_3$ alkyl. In some embodiments of the compounds of Formula I, $R_{17}$ is $C_4$ alkyl. In some embodiments of the compounds of Formula I, $R_{17}$ is $C_5$ alkyl. In some embodiments of the compounds of Formula I, $R_{17}$ is $C_6$ alkyl.

In some embodiments of the compounds of Formula I, $R_{20}$ is oxo or $C_{1-6}$ alkyl. In another embodiment, $R_{20}$ is oxo. In another embodiment, $R_{20}$ is $C_{1-6}$ alkyl. In some embodiments of the compounds of Formula I, $R_{20}$ is $C_{1-5}$ alkyl. In some embodiments of the compounds of Formula I, $R_{20}$ is $C_{1-4}$ alkyl. In some embodiments of the compounds of Formula I, $R_{20}$ is $C_{2-6}$ alkyl. In some embodiments of the compounds of Formula I, $R_{20}$ is $C_1$ alkyl. In some embodiments of the compounds of Formula I, $R_{20}$ is $C_2$ alkyl. In some embodiments of the compounds of Formula I, $R_{20}$ is $C_3$ alkyl. In some embodiments of the compounds of Formula I, $R_{20}$ is $C_4$ alkyl. In some embodiments of the compounds of Formula I, $R_{20}$ is $C_5$ alkyl. In some embodiments of the compounds of Formula I, $R_{20}$ is $C_6$ alkyl.

In some embodiments of the compounds of Formula I, $R_{21}$ is —H or $C_{1-6}$ alkyl. In another embodiment, $R_{21}$ is —H. In another embodiment, $R_{21}$ is $C_{1-6}$ alkyl. In some embodiments of the compounds of Formula I, $R_{21}$ is $C_{1-5}$ alkyl. In some embodiments of the compounds of Formula I, $R_{21}$ is $C_{1-4}$ alkyl. In some embodiments of the compounds of Formula I, $R_{21}$ is $C_{2-6}$ alkyl. In some embodiments of the compounds of Formula I, $R_{21}$ is $C_1$ alkyl. In some embodiments of the compounds of Formula I, $R_{21}$ is $C_2$ alkyl. In some embodiments of the compounds of Formula I, $R_{21}$ is $C_3$ alkyl. In some embodiments of the compounds of Formula I, $R_{21}$ is $C_4$ alkyl. In some embodiments of the compounds of Formula I, $R_{21}$ is $C_5$ alkyl. In some embodiments of the compounds of Formula I, $R_{21}$ is $C_6$ alkyl.

In other embodiments of the compounds of Formula I, $R_{23}$ is $C_{1-6}$ alkyl. In another embodiment, $R_{23}$ is $C_{1-6}$ alkyl optionally substituted with one or more —N($C_{1-6}$ alkyl)$_2$.

In one embodiment of the compounds of Formula I, two $R_{23}$ together form a heterocyclyl. In one embodiment of the compounds of Formula I, two $R_{23}$ together form a heterocyclyl wherein the heterocyclyl is optionally substituted by $C_{1-6}$ alkyl.

In some embodiments of the compounds of Formula I, $R_{26}$ is —H or $C_{1-6}$ alkyl. In another embodiment, $R_{26}$ is —H. In another embodiment, $R_{26}$ is $C_{1-6}$ alkyl. In some embodiments of the compounds of Formula I, $R_{26}$ is $C_{1-5}$ alkyl. In some embodiments of the compounds of Formula I, $R_{26}$ is $C_{1-4}$ alkyl. In some embodiments of the compounds of Formula I, $R_{26}$ is $C_{2-6}$ alkyl. In some embodiments of the compounds of Formula I, $R_{26}$ is $C_1$ alkyl. In some embodiments of the compounds of Formula I, $R_{26}$ is $C_2$ alkyl. In some embodiments of the compounds of Formula I, $R_{26}$ is $C_3$ alkyl. In some embodiments of the compounds of Formula I, $R_{26}$ is $C_4$ alkyl. In some embodiments of the compounds of Formula I, $R_{26}$ is $C_5$ alkyl. In some embodiments of the compounds of Formula I, $R_{26}$ is $C_6$ alkyl.

In some embodiments of the compounds of Formula I, $R_{27}$ is $C_{1-6}$ alkyl, heterocyclyl, cycloalkyl. In some embodiments of the compounds of Formula I, $R_{27}$ is $C_{1-6}$ alkyl. In some embodiments of the compounds of Formula I, $R_{27}$ is heterocyclyl or cycloalkyl. In some embodiments of the compounds of Formula I, $R_{27}$ is heterocyclyl. In some embodiments of the compounds of Formula I, $R_{27}$ is cycloalkyl. In some embodiments of the compounds of Formula I, $R_{27}$ is $C_{1-6}$ alkyl, heterocyclyl, cycloalkyl, wherein the alkyl, heterocyclyl, cycloalkyl is optionally substituted with one or more halogen, —CN, —C(O)OH, —OH, —NH$_2$. In some embodiments of the compounds of Formula I, $R_{27}$ is $C_{1-6}$ alkyl optionally substituted with one or more halogen, —CN, —C(O)OH, —OH, —NH$_2$. In some embodiments of the compounds of Formula I, $R_{27}$ is heterocyclyl optionally substituted with one or more halogen, —CN, —C(O)OH, —OH, —NH$_2$. In some embodiments of the compounds of Formula I, $R_{27}$ is cycloalkyl optionally substituted with one or more halogen, —CN, —C(O)OH, —OH, —NH$_2$.

In one embodiment, o is 1, 2, 3, or 4. In another embodiment o is 1 or 2. In another embodiment o is 1. In another embodiment o is 2. In another embodiment o is 3. In another embodiment o is 4.

In one embodiment, $R_8$ is not methoxy.

In one embodiment of the compounds of Formula I, A is aryl, B is heteroaryl, $X_1$ is $C(R_5)$, $X_2$ is $C(R_5)$, W is $C(R_6)$, and $R_1$ is —N(R$_2$)C(O)R$_3$.

In one embodiment of the compounds of Formula I, A is aryl, B is heteroaryl, $X_1$ is $C(R_5)$, $X_2$ is $C(R_5)$, W is $C(R_6)$, and $R_1$ is —C(O)N(R$_2$)(R$_3$).

In one embodiment of the compounds of Formula I, A is aryl, B is heteroaryl, $X_1$ is $C(R_5)$, $X_2$ is $C(R_5)$, W is $C(R_6)$, and $R_1$ is —P(O)(R$_2$)(R$_3$).

In one embodiment of the compounds of Formula I, A is aryl, B is heteroaryl, $X_1$ is $C(R_5)$, $X_2$ is $C(R_5)$, W is $C(R_6)$, and $R_1$ is heteroaryl.

In one embodiment of the compounds of Formula I, A is aryl, B is heteroaryl, $X_1$ is $C(R_5)$, $X_2$ is $C(R_5)$, W is $C(R_6)$, and $R_1$ is heteroaryl optionally substituted with one or more $R_7$.

In one embodiment of the compounds of Formula I, A is aryl, B is heteroaryl, $X_1$ is $C(R_5)$, $X_2$ is N, W is $C(R_6)$, and $R_1$ is —N(R$_2$)C(O)R$_3$.

In one embodiment of the compounds of Formula I, A is aryl, B is heteroaryl, $X_1$ is $C(R_5)$, $X_2$ is N, W is $C(R_6)$, and $R_1$ is —C(O)N(R$_2$)(R$_3$).

In one embodiment of the compounds of Formula I, A is aryl, B is heteroaryl, $X_1$ is $C(R_5)$, $X_2$ is N, W is $C(R_6)$, and $R_1$ is —P(O)(R$_2$)(R$_3$).

In one embodiment of the compounds of Formula I, A is aryl, B is heteroaryl, $X_1$ is $C(R_5)$, $X_2$ is N, W is $C(R_6)$, and $R_1$ is heteroaryl.

In one embodiment of the compounds of Formula I, A is aryl, B is heteroaryl, $X_1$ is $C(R_5)$, $X_2$ is N, W is $C(R_6)$, and $R_1$ is heteroaryl optionally substituted with one or more $R_7$.

In one embodiment of the compounds of Formula I, A is aryl, B is heteroaryl optionally substituted with one or two $R_8$, $X_1$ is $C(R_5)$, $X_2$ is $C(R_5)$, W is $C(R_6)$, and $R_1$ is —N(R$_2$)C(O)R$_3$.

In one embodiment of the compounds of Formula I, A is aryl, B is heteroaryl optionally substituted with one or two $R_8$, $X_1$ is $C(R_5)$, $X_2$ is $C(R_5)$, W is $C(R_6)$, and $R_1$ is —C(O)N(R$_2$)(R$_3$).

In one embodiment of the compounds of Formula I, A is aryl, B is heteroaryl optionally substituted with one or two $R_8$, $X_1$ is $C(R_5)$, $X_2$ is $C(R_5)$, W is $C(R_6)$, and $R_1$ is —P(O)(R$_2$)(R$_3$).

In one embodiment of the compounds of Formula I, A is aryl, B is heteroaryl optionally substituted with one or two $R_8$, $X_1$ is $C(R_5)$, $X_2$ is $C(R_5)$, W is $C(R_6)$, and $R_1$ is heteroaryl.

In one embodiment of the compounds of Formula I, A is aryl, B is heteroaryl optionally substituted with one or two $R_8$, $X_1$ is $C(R_5)$, $X_2$ is $C(R_5)$, W is $C(R_6)$, and $R_1$ is heteroaryl optionally substituted with one or more $R_7$.

In one embodiment of the compounds of Formula I, A is aryl, B is heteroaryl optionally substituted with one or two $R_8$, $X_1$ is $C(R_5)$, $X_2$ is N, W is $C(R_6)$, and $R_1$ is —N(R$_2$)C(O)R$_3$.

In one embodiment of the compounds of Formula I, A is aryl, B is heteroaryl optionally substituted with one or two $R_8$, $X_1$ is $C(R_5)$, $X_2$ is N, W is $C(R_6)$, and $R_1$ is —C(O)N(R$_2$)(R$_3$).

In one embodiment of the compounds of Formula I, A is aryl, B is heteroaryl optionally substituted with one or two $R_8$, $X_1$ is $C(R_5)$, $X_2$ is N, W is $C(R_6)$, and $R_1$ is —P(O)(R$_2$)(R$_3$).

In one embodiment of the compounds of Formula I, A is aryl, B is heteroaryl optionally substituted with one or two $R_8$, $X_1$ is $C(R_5)$, $X_2$ is N, W is $C(R_6)$, and $R_1$ is heteroaryl.

In one embodiment of the compounds of Formula I, A is aryl, B is heteroaryl optionally substituted with one or two $R_8$, $X_1$ is $C(R_5)$, $X_2$ is N, W is $C(R_6)$, and $R_1$ is heteroaryl optionally substituted with one or more $R_7$.

In one embodiment of the compounds of Formula I, A is aryl, B is heteroaryl optionally substituted with one or more $R_8$, wherein $R_8$ is heterocyclyl, or —N(R$_9$)(R$_{10}$), —OR$_{10}$, $X_1$ is $C(R_5)$, $X_2$ is $C(R_5)$, W is $C(R_6)$, and $R_1$ is —N(R$_2$)C(O)R$_3$.

In one embodiment of the compounds of Formula I, A is aryl, B is heteroaryl optionally substituted with one or more $R_8$, wherein $R_8$ is heterocyclyl, or —N(R$_9$)(R$_{10}$), —OR$_{10}$, wherein the heterocyclyl, is optionally substituted with one or more $R_{15}$, $X_1$ is $C(R_5)$, $X_2$ is $C(R_5)$, W is $C(R_6)$, and $R_1$ is —N(R$_2$)C(O)R$_3$.

In one embodiment of the compounds of Formula I, A is aryl, B is heteroaryl optionally substituted with one or more $R_8$, wherein $R_8$ is heterocyclyl, or —N(R$_9$)(R$_{10}$), —OR$_{10}$, wherein the heterocyclyl, is optionally substituted with one or more $R_{15}$, $X_1$ is $C(R_5)$, $X_2$ is $C(R_5)$, W is $C(R_6)$, and $R_1$ is —N(R$_2$)C(O)R$_3$, wherein $R_2$ and $R_3$ when taken together with the atom to which they are each attached form a heterocycle optionally substituted with one or more $R_4$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, $X_1$ is $C(R_5)$, $X_2$ is N, W is $C(R_6)$, and $R_1$ is —$N(R_2)C(O)R_3$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, wherein the heterocyclyl, is optionally substituted with one or more $R_{15}$, $X_1$ is $C(R_5)$, $X_2$ is N, W is $C(R_6)$, and $R_1$ is —$N(R_2)C(O)R_3$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, wherein the heterocyclyl, is optionally substituted with one or more $R_{15}$, $X_1$ is $C(R_5)$, $X_2$ is N, W is $C(R_6)$, and $R_1$ is —$N(R_2)C(O)R_3$, wherein $R_2$ and $R_3$ when taken together with the atom to which they are each attached form a heterocycle optionally substituted with one or more $R_4$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, wherein the heterocyclyl, is optionally substituted with one or more $R_{15}$, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, $X_1$ is $C(R_5)$, $X_2$ is N, W is $C(R_6)$, and $R_1$ is —$C(O)N(R_2)(R_3)$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, wherein the heterocyclyl, is optionally substituted with one or more $R_{15}$, $X_1$ is $C(R_5)$, $X_2$ is N, W is $C(R_6)$, and $R_1$ is —$C(O)N(R_2)(R_3)$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, $X_1$ is $C(R_5)$, $X_2$ is $C(R_5)$, W is $C(R_6)$, and $R_1$ is —$P(O)(R_2)(R_3)$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, wherein the heterocyclyl, is optionally substituted with one or more $R_{15}$, $X_1$ is $C(R_5)$, $X_2$ is $C(R_5)$, W is $C(R_6)$, and $R_1$ is —$P(O)(R_2)(R_3)$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, $X_1$ is $C(R_5)$, $X_2$ is N, W is $C(R_6)$, and $R_1$ is —$P(O)(R_2)(R_3)$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, wherein the heterocyclyl, is optionally substituted with one or more $R_{15}$, $X_1$ is $C(R_5)$, $X_2$ is N, W is $C(R_6)$, and $R_1$ is —$P(O)(R_2)(R_3)$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, $X_1$ is $C(R_5)$, $X_2$ is $C(R_5)$, W is $C(R_6)$, and $R_1$ is heteroaryl.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, wherein the heterocyclyl, is optionally substituted with one or more $R_{15}$, $X_1$ is $C(R_5)$, $X_2$ is $C(R_5)$, W is $C(R_6)$, and $R_1$ is heteroaryl.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, $X_1$ is $C(R_5)$, $X_2$ is N, W is $C(R_6)$, and $R_1$ is heteroaryl.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, wherein the heterocyclyl, is optionally substituted with one or more $R_{15}$, $X_1$ is $C(R_5)$, $X_2$ is N, W is $C(R_6)$, and $R_1$ is heteroaryl.

In one embodiment of the compounds of Formula I, A is aryl, B is heteroaryl optionally substituted with one or more $R_8$, wherein $R_8$ is heterocyclyl, or —$N(R_9)(R_{10})$, —$ORIO$, $X_1$ is $C(R_5)$, $X_2$ is $C(R_5)$, W is $C(R_6)$, and $R_1$ is heteroaryl optionally substituted with one or more $R_7$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, wherein the heterocyclyl, is optionally substituted with one or more $R_{15}$, $X_1$ is $C(R_5)$, $X_2$ is $C(R_5)$, W is $C(R_6)$, and $R_1$ is heteroaryl optionally substituted with one or more $R_7$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, $X_1$ is $C(R_5)$, $X_2$ is N, W is $C(R_6)$, and $R_1$ is heteroaryl optionally substituted with one or more $R_7$.

In one embodiment of the compounds of Formula I, A is aryl, B is heteroaryl optionally substituted with one or more $R_8$, wherein $R_8$ is heterocyclyl, or —$N(R_9)(R_{10})$, —$OR_{10}$, wherein the heterocyclyl, is optionally substituted with one or more $R_{15}$, $X_1$ is $C(R_5)$, $X_2$ is N, W is $C(R_6)$, and $R_1$ is heteroaryl optionally substituted with one or more $R_7$.

In one embodiment of the compounds of Formula I, A is aryl, B is heteroaryl optionally substituted with one or more $R_8$, wherein two $R_8$ groups, together with the atoms to which they are attached, form a heterocyclyl, optionally substituted with one or more $R_{15}$, $X_1$ is $C(R_5)$, $X_2$ is N, W is $C(R_6)$, and $R_1$ is —$N(R_2)C(O)R_3$.

In one embodiment of the compounds of Formula I, A is aryl, B is heteroaryl optionally substituted with one or more $R_8$, two $R_8$ groups, together with the atoms to which they are attached, form a heterocyclyl, optionally substituted with one or more $R_{15}$, $X_1$ is $C(R_5)$, $X_2$ is N, W is $C(R_6)$, and $R_1$ is —$N(R_2)C(O)R_3$, wherein $R_2$ and $R_3$ when taken together with the atom to which they are each attached form a heterocycle optionally substituted with one or more $R_4$.

In one embodiment of the compounds of Formula I, A is aryl, B is heteroaryl optionally substituted with one or more $R_8$, wherein two $R_8$ groups, together with the atoms to which they are attached, form a heterocyclyl, optionally substituted with one or more $R_{15}$, $X_1$ is $C(R_5)$, $X_2$ is $C(R_5)$, W is $C(R_6)$, and $R_1$ is —$C(O)N(R_2)(R_3)$.

In one embodiment of the compounds of Formula I, A is aryl, B is heteroaryl optionally substituted with one or more $R_8$, wherein two $R_8$ groups, together with the atoms to which they are attached, form a heterocyclyl, optionally substituted with one or more $R_{15}$, $X_1$ is $C(R_5)$, $X_2$ is N, W is $C(R_6)$, and $R_1$ is —$C(O)N(R_2)(R_3)$.

In one embodiment of the compounds of Formula I, A is aryl, B is heteroaryl optionally substituted with one or more $R_8$, wherein two $R_8$ groups, together with the atoms to which they are attached, form a heterocyclyl, optionally substituted with one or more $R_{15}$, $X_1$ is $C(R_5)$, $X_2$ is $C(R_5)$, W is $C(R_6)$, and $R_1$ is —$P(O)(R_2)(R_3)$.

In one embodiment of the compounds of Formula I, A is aryl, B is heteroaryl optionally substituted with one or more $R_8$, wherein two $R_8$ groups, together with the atoms to which they are attached, form a heterocyclyl, optionally substituted with one or more $R_{15}$, $X_1$ is $C(R_5)$, $X_2$ is N, W is $C(R_6)$, and $R_1$ is —P(O)($R_2$)($R_3$).

In one embodiment of the compounds of Formula I, A is aryl, B is heteroaryl optionally substituted with one or more $R_8$, wherein two $R_8$ groups, together with the atoms to which they are attached, form a heterocyclyl, optionally substituted with one or more $R_{15}$, $X_1$ is $C(R_5)$, $X_2$ is $C(R_5)$, W is $C(R_6)$, and $R_1$ is heteroaryl.

In one embodiment of the compounds of Formula I, A is aryl, B is heteroaryl optionally substituted with one or more $R_8$, wherein two $R_8$ groups, together with the atoms to which they are attached, form a heterocyclyl, optionally substituted with one or more $R_{15}$, $X_1$ is $C(R_5)$, $X_2$ is N, W is $C(R_6)$, and $R_1$ is heteroaryl.

In one embodiment of the compounds of Formula I, A is aryl, B is heteroaryl optionally substituted with one or more $R_8$, wherein two $R_8$ groups, together with the atoms to which they are attached, form a heterocyclyl, optionally substituted with one or more $R_{15}$, $X_1$ is $C(R_5)$, $X_2$ is $C(R_5)$, W is $C(R_6)$, and $R_1$ is heteroaryl optionally substituted with one or more $R_7$.

In one embodiment of the compounds of Formula I, A is aryl, B is heteroaryl optionally substituted with one or more $R_8$, wherein two $R_8$ groups, together with the atoms to which they are attached, form a heterocyclyl, optionally substituted with one or more $R_{15}$, $X_1$ is $C(R_5)$, $X_2$ is N, W is $C(R_6)$, and $R_1$ is heteroaryl optionally substituted with one or more $R_7$.

Non-limiting illustrative compounds of the present disclosure include:

- 2-[(2-{[(6S)-3-oxo-8-oxa-2,10-diazatricyclo[7.4.0.0$^{2,6}$]trideca-1(9),10,12-trien-12-yl]amino}-5-[4-(2-oxopyrrolidin-1-yl)phenyl]pyrimidin-4-yl)amino]acetic acid;
- (6S)-12-[(4-{methyl[(3S)-oxolan-3-yl]amino}-5-[4-(2-oxopyrrolidin-1-yl)phenyl]pyrimidin-2-yl)amino]-8-oxa-2,10-diazatricyclo[7.4.0.0$^{2,6}$]trideca-1(13),9,11-trien-3-one;
- (6S)-12-({4-[methyl(oxolan-3-yl)amino]-5-[4-(2-oxopyrrolidin-1-yl)phenyl]pyrimidin-2-yl}amino)-8-oxa-2,10-diazatricyclo[7.4.0.0$^{2,6}$]trideca-1(13),9,11-trien-3-one;
- (6S)-12-[(4-{methyl[(1r,3r)-3-hydroxycyclobutyl]amino}-5-[4-(2-oxopyrrolidin-1-yl)phenyl]pyrimidin-2-yl)amino]-8-oxa-2,10-diazatricyclo[7.4.0.0$^{2,6}$]trideca-1(13),9,11-trien-3-one;
- 2-(dimethylamino)ethyl 7-({4-methoxy-5-[4-(2-oxopyrrolidin-1-yl)phenyl]pyrimidin-2-yl}amino)-1H,2H,3H-pyrido[2,3-b][1,4]oxazine-1-carboxylate;
- (6S)-12-({4-[2-(morpholin-4-yl)ethoxy]-5-[4-(2-oxopyrrolidin-1-yl)phenyl]pyrimidin-2-yl}amino)-8-oxa-2,10-diazatricyclo[7.4.0.0$^{2,6}$]trideca-1(9),10,12-trien-3-one;
- (6S)-12-[(4-{methyl[(3R)-oxolan-3-yl]amino}-5-[4-(2-oxopyrrolidin-1-yl)phenyl]pyrimidin-2-yl)amino]-8-oxa-2,10-diazatricyclo[7.4.0.0$^{2,6}$]trideca-1(13),9,11-trien-3-one;
- (6S)-12-({5-[4-(4-methyl-4H-1,2,4-triazol-3-yl)phenyl]-4-(prop-1-en-2-yl)pyridin-2-yl}amino)-8-oxa-2,10-diazatricyclo[7.4.0.0$^{2,6}$]trideca-1(13),9,11-trien-3-one;
- N-cyclopropyl-4-(4-methoxy-2-{[(6S)-3-oxo-8-oxa-2,10-diazatricyclo[7.4.0.0$^{2,6}$]trideca-1(9),10,12-trien-12-yl]amino}pyrimidin-5-yl)-N-methylbenzamide;
- 3-methyl-1-(2-{[(6S)-3-oxo-8-oxa-2,10-diazatricyclo[7.4.0.0$^{2,6}$]trideca-1(13),9,11-trien-12-yl]amino}-5-[4-(2-oxopyrrolidin-1-yl)phenyl]pyrimidin-4-yl)azetidine-3-carbonitrile;
- 12-({4-methoxy-5-[4-(2-oxopyrrolidin-1-yl)phenyl]pyrimidin-2-yl}amino)-4-[2-(morpholin-4-yl)ethyl]-8-oxa-2,4,10-triazatricyclo[7.4.0.0$^{2,6}$]trideca-1(9),10,12-trien-3-one;
- 1-{4-[2-({2H,3H-[1,4]dioxino[2,3-b]pyridin-7-yl}amino)-4-{methyl[(1r,3r)-3-hydroxycyclobutyl]amino}pyrimidin-5-yl]phenyl}pyrrolidin-2-one;
- 2-(dimethylamino)ethyl 7-({5-[4-(5-methyl-1H-1,2,3-triazol-1-yl)phenyl]pyrimidin-2-yl}amino)-1H,2H,3H-pyrido[2,3-b][1,4]oxazine-1-carboxylate;
- (6S)-12-({5-[4-(2-oxopyrrolidin-1-yl)phenyl]-4-(trifluoromethyl)pyrimidin-2-yl}amino)-8-oxa-2,10-diazatricyclo[7.4.0.0$^{2,6}$]trideca-1(9),10,12-trien-3-one;
- 2-(dimethylamino)ethyl 7-({5-[4-(dimethylcarbamoyl)phenyl]-4-methoxypyrimidin-2-yl}amino)-1H,2H,3H-pyrido[2,3-b][1,4]oxazine-1-carboxylate; 1-{4-[2-({5-[4-(dimethylamino)piperidin-1-yl]pyridin-3-yl}amino)-4-methoxypyrimidin-5-yl]phenyl}pyrrolidin-2-one;
- N-{5-[4-(dimethylamino)piperidin-1-yl]pyridin-3-yl}-4-methoxy-5-[4-(4-methylpyridazin-3-yl)phenyl]pyrimidin-2-amine;
- 4-[2-({2H,3H-[1,4]dioxino[2,3-b]pyridin-7-yl}amino)-4-{methyl[(1s,3s)-3-hydroxycyclobutyl]amino}pyrimidin-5-yl]-N,N-dimethylbenzamide;
- 1-{4-[2-({1-[2-(dimethylamino)acetyl]-1H,2H,3H-pyrido[2,3-b][1,4]oxazin-7-yl}amino)-4-methoxypyrimidin-5-yl]phenyl}pyrrolidin-2-one;
- 2-(dimethylamino)-1-[7-({5-[4-(5-methyl-1H-1,2,3-triazol-1-yl)phenyl]pyrimidin-2-yl}amino)-1H,2H,3H-pyrido[2,3-b][1,4]oxazin-1-yl]ethan-1-one;
- (6S)-12-({5-[3-fluoro-4-(2-oxopyrrolidin-1-yl)phenyl]-4-[(3-hydroxyoxetan-3-yl)methyl]pyrimidin-2-yl}amino)-8-oxa-2,10-diazatricyclo[7.4.0.0$^{2,6}$]trideca-1(9),10,12-trien-3-one;
- 2-(diethylamino)ethyl 7-[(5-{4-[(2R)-2-methyl-5-oxopyrrolidin-1-yl]phenyl}pyrimidin-2-yl)amino]-1H,2H,3H-pyrido[2,3-b][1,4]oxazine-1-carboxylate;
- 2-(diethylamino)ethyl 7-({5-[4-(2-oxopyrrolidin-1-yl)phenyl]pyrimidin-2-yl}amino)-1H,2H,3H-pyrido[2,3-b][1,4]oxazine-1-carboxylate;
- N-[2-(diethylamino)ethyl]-7-[(4-methoxy-5-{4-[(2R)-2-methyl-5-oxopyrrolidin-1-yl]phenyl}pyrimidin-2-yl)amino]-N-methyl-1H,2H,3H-pyrido[2,3-b][1,4]oxazine-1-carboxamide;
- N-[2-(diethylamino)ethyl]-N-methyl-7-[(5-{4-[(2R)-2-methyl-5-oxopyrrolidin-1-yl]phenyl}pyrimidin-2-yl)amino]-1H,2H,3H-pyrido[2,3-b][1,4]oxazine-1-carboxamide;
- 1-{4-[2-({1-[2-(diethylamino)ethyl]-1H,2H,3H-pyrido[2,3-b][1,4]oxazin-7-yl}amino)-4-methoxypyrimidin-5-yl]phenyl}pyrrolidin-2-one;
- (6S)-12-({5-[4-(dimethylphosphoryl)phenyl]pyridin-2-yl}amino)-8-oxa-2,10-diazatricyclo[7.4.0.0$^{2,6}$]trideca-1(9),10,12-trien-3-one;
- 2-{4-[5-({4-methoxy-5-[4-(4-methylpyridazin-3-yl)phenyl]pyrimidin-2-yl}amino)pyridin-3-yl]piperazin-1-yl}ethan-1-ol;
- N-[2-(diethylamino)ethyl]-7-[(5-{4-[(2R)-2-methyl-5-oxopyrrolidin-1-yl]phenyl}pyrimidin-2-yl)amino]-1H,2H,3H-pyrido[2,3-b][1,4]oxazine-1-carboxamide;
- 1-(4-{2-[(5-{[2-(4-ethylpiperazin-1-yl)-2-oxoethyl](methyl)amino}pyridin-3-yl)amino]-4-methoxypyrimidin-5-yl}phenyl)pyrrolidin-2-one;
- N3-[2-(3,3-difluoropyrrolidin-1-yl)ethyl]-N5-{4-methoxy-5-[4-(4-methylpyridazin-3-yl)phenyl]pyrimidin-2-yl}-N3-methylpyridine-3,5-diamine;

1-(4-{2-[(5-{[2-(4,4-difluoropiperidin-1-yl)ethyl](methyl) amino}pyridin-3-yl)amino]-4-methoxypyrimidin-5-yl}phenyl)pyrrolidin-2-one;

1-(4-{2-[(5-{[2-(3,3-difluoropyrrolidin-1-yl)ethyl](methyl) amino}pyridin-3-yl)amino]-4-methoxypyrimidin-5-yl}phenyl)pyrrolidin-2-one;

N-{5-[(3R)-3-(dimethylamino)pyrrolidin-1-yl]pyridin-3-yl}-4-methoxy-5-[4-(4-methylpyridazin-3-yl)phenyl]pyrimidin-2-amine;

1-{4-[2-({5-[(3R)-3-(dimethylamino)pyrrolidin-1-yl]pyridin-3-yl}amino)-4-methoxypyrimidin-5-yl] phenyl}pyrrolidin-2-one;

1-(4-{4-methoxy-2-[(5-{methyl[2-oxo-2-(piperazin-1-yl) ethyl]amino}pyridin-3-yl)amino]pyrimidin-5-yl}phenyl) pyrrolidin-2-one;

N-{5-[(3S)-3-(dimethylamino)pyrrolidin-1-yl]pyridin-3-yl}-4-methoxy-5-[4-(4-methylpyridazin-3-yl)phenyl]pyrimidin-2-amine;

1-{4-[2-({5-[(3S)-3-(dimethylamino)pyrrolidin-1-yl]pyridin-3-yl}amino)-4-methoxypyrimidin-5-yl] phenyl}pyrrolidin-2-one;

1-(4-{4-methoxy-2-[(5-{methyl[3-oxo-3-(piperazin-1-yl) propyl]amino}pyridin-3-yl)amino]pyrimidin-5-yl}phenyl)pyrrolidin-2-one;

N-{5-[2-(3,3-difluoropyrrolidin-1-yl)ethoxy]pyridin-3-yl}-4-methoxy-5-[4-(4-methylpyridazin-3-yl)phenyl]pyrimidin-2-amine; and 1-{4-[2-({5-[2-(3,3-difluoropyrrolidin-1-yl)ethoxy]pyridin-3-yl}amino)-4-methoxypyrimidin-5-yl] phenyl}pyrrolidin-2-one.

It should be understood that all isomeric forms are included within the present invention, including mixtures thereof. If the compound contains a double bond, the substituent may be in the E or Z configuration. If the compound contains a di-substituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of PI5P4K. In one embodiment, the compounds of the present invention are inhibitors of PI5P4K.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "*Protective Groups in Organic Synthesis*", Third edition, Wiley, New York 1999). These groups are removed at a convenient stage of the compound synthesis using methods that are readily apparent to those skilled in the art. The selection processes, as well as the reaction conditions and order will be readily apparent to those skilled in the art and they will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-lnterscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Scheme 1 which comprise different sequences of assembling intermediates or compounds (II). Starting materials are either commercially available or made by known procedures in the reported literature or as illustrated below.

A compound of formula (I) may be obtained (Scheme 1) by starting from, for example, a compound of formula (II), wherein LG represents a leaving group including, but not limited to, halogen (e.g., chlorine, bromine or iodine), or an alkyl-sulfonate, aryl-sulfonate or haloalkyl-sulfonate (e.g., triflate), and reacting said compound (II) with a compound of formula B—NH$_2$, wherein B—NH$_2$ is defined below and represents a cyclic amine either as free base or a salt (e.g., HCl, TFA or acetic acid), optionally under the influence of a transition metal catalyst as described in for example *Metal-Catalyzed Cross-Coupling Reactions, 2$^{nd}$, Completely Revised and Enlarged Edition* by A. de Meijere and F. Diederich, Wiley VCH, 2004.

Scheme 1

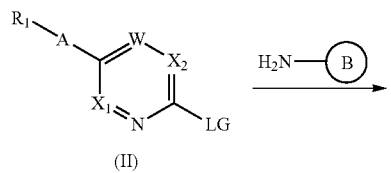

(II)

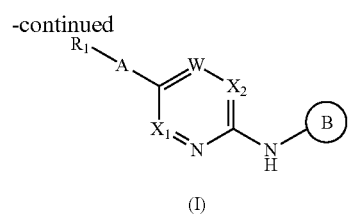

(I)

The reaction may be carried out by coupling of a compound of formula (II), with an appropriate amine of formula B—NH$_2$. The reaction may also be carried out using a suitable metal catalyst including, but not limited to, a palladium catalyst, for example, (di-tert-butylphosphino)ferrocene palladium (II) dichloride, tetrakis(triphenylphosphine)palladium (0), palladium (II) (diphenylphosphino)ferrocene dichloride, palladium(II) acetate or bis(dibenzylideneacetone) palladium (0). Optionally a suitable ligand, for example, triphenylphosphine, tri-tert-butylphosphine or 2-(dicyclohexylphosphino)biphenyl or 2-dicyclohexylphosphino-2',4',6'-triisopropylbiphenyl is employed. Suitable bases, including an alkyl amine base, (e.g., triethyl amine), an alkali metal or alkaline earth metal carbonate or hydroxide, or phosphate base, (e.g., potassium carbonate, sodium carbonate, cesium carbonate, sodium hydroxide, or potassium phosphate), may be used in the reaction. Said reaction may be performed at a temperature range between +20° C. and +160° C., in suitable solvents, including, without limitation, toluene, tetrahydrofuran, 2-methyl-tetrahydrofuran, 1,4-dioxane, 1,2-dimethoxyethane, acetonitrile, water, ethanol, N,N-dimethylacetamide or N,N-dimethylformamide, or mixtures thereof. If enantiomerically pure or enriched compound (II) is used in this reaction, an enantiomerically pure or enantiomerically enriched compound (I) is obtained.

Compounds of formula (II) and B—NH$_2$ may be commercially available compounds, or known in the literature, or they are prepared by standard processes known in the art. A compound of formula (I), (II) or B—NH$_2$ may be separated into its enantiomers by standard processes known in the art by for example chromatography on a chiral stationary phase.

Methods of Using the Disclosed Compounds

Another aspect of the invention relates to a method of treating a disease or disorder associated with modulation of PI5P4K. The method comprises administering to a patient in need of a treatment for diseases or disorders associated with modulation of PI5P4K an effective amount the compositions and compounds of Formula (I).

In another aspect, the present invention is directed to a method of inhibiting PI5P4K. The method involves administering to a patient in need thereof an effective amount of a compound of Formula (I).

Another aspect of the present invention relates to a method of treating, preventing, inhibiting or eliminating a disease or disorder in a patient associated with the inhibition of PI5P4K, the method comprising administering to a patient in need thereof an effective amount of a compound of Formula (I). In one embodiment, the disease may be, but not limited to, cancer or cell proliferative disorder, a metabolic disorder, neurodegenerative disease, and an inflammatory disease.

The present invention also relates to the use of an inhibitor of PI5P4K for the preparation of a medicament used in the treatment, prevention, inhibition or elimination of a disease or condition mediated by PI5P4K, wherein the medicament comprises a compound of Formula (I).

In another aspect, the present invention relates to a method for the manufacture of a medicament for treating, preventing, inhibiting, or eliminating a disease or condition mediated by PI5P4K, wherein the medicament comprises a compound of Formula (I).

Another aspect of the present invention relates to a compound of Formula (I) for use in the manufacture of a medicament for treating a disease associated with inhibiting PI5P4K.

In another aspect, the present invention relates to the use of a compound of Formula (I) in the treatment of a disease associated with inhibiting PI5P4K.

Another aspect of the invention relates to a method of treating cancer. The method comprises administering to a patient in need thereof an effective amount of a compound of Formula (I).

In another aspect of the invention, the method relates to treating a cell proliferative disease. The method comprises administering to a patient in need thereof an effective amount of a compound of Formula (I).

In yet another aspect, the present invention relates to a method of treating a neurodegenerative disease. The method comprises administering to a patient in need thereof an effective amount of a compound of Formula (I).

In another aspect, the present invention relates to a method of treating an inflammatory disease or condition. The method comprises administering to a patient in need thereof an effective amount of a compound of Formula (I).

Another aspect of the invention relates to a method of inducing cell cycle arrest, apoptosis in tumor cells, and/or enhanced tumor-specific T cell immunity. The method comprises contacting the cells with an effective amount of a compound of Formula (I).

In one embodiment, the present invention relates to the use of an inhibitor of PI5P4K for the preparation of a medicament used in treatment, prevention, inhibition or elimination of a disease or disorder associated with cancer or cell proliferative disorder, a metabolic disorder, neurodegenerative disease, and an inflammatory disease.

In another embodiment, the present invention relates to a compound of Formula (I) or a pharmaceutical composition comprising a compound of the present invention and a pharmaceutically acceptable carrier used for the treatment of cancers or cell proliferative disorders including, but not limited to, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In another embodiment, the present invention relates to a compound of Formula (I) or a pharmaceutical composition comprising a compound of the present invention and a pharmaceutically acceptable carrier used for the treatment of neurodegenerative diseases including, but not limited to, brain trauma, spinal cord trauma, trauma to the peripheral nervous system, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffman disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia, age-related dementia, vascular dementia, diffuse white matter disease (Binswanger's disease), dementia of endocrine or metabolic origin, dementia of head trauma and diffuse brain damage, dementia pugilistica or frontal lobe dementia, neurodegenerative disorders resulting from cerebral ischemia or infarction including embolic occlusion and thrombotic occlusion as well as intracranial hemorrhage of any type, intracranial and intravertebral lesions, hereditary cerebral angiopathy, normeuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis.

In another embodiment, the present invention relates to a compound of Formula (I) or a pharmaceutical composition comprising a compound of the present invention and a pharmaceutically acceptable carrier used for the treatment of inflammatory disease. In some embodiments, the inflammatory disease is associated with a metabolic disorder. In some embodiments the treated inflammation is associated with, but not limited to, Type II diabetes, insulin resistance cardiovascular disease, arrhythmia, atherosclerosis, coronary artery disease, hypertriglyceridemia, dyslipidemia, retinopathy, nephropathy, neuropathy, obesity, and macular edema.

In yet another embodiment, the present invention relates to a compound of Formula (I) or a pharmaceutical composition comprising a compound of the present invention and a pharmaceutically acceptable carrier used for the treatment of a metabolic disease including, but not limited, Type II diabetes, insulin resistance cardiovascular disease, arrhythmia, atherosclerosis, coronary artery disease, hypertriglyceridemia, dyslipidemia, retinopathy, nephropathy, neuropathy, obesity, and macular edema.

In another embodiment, the present invention relates to a compound of Formula (I) or a pharmaceutical composition comprising a compound of the present invention and a pharmaceutically acceptable carrier used for the treatment of inflammatory disease associated with inflammatory disease. In some embodiments the treated inflammation is associated with, but not limited to, ileitis, ulcerative colitis, Barrett's syndrome, or Crohn's disease.

In some embodiments, the patient is selected for treatment based on gene amplification and/or elevated tumor expression of PI5P4K. In other embodiments, the patient is selected for treatment based on gene amplification and/or elevated tumor expression of PI5P4Kα gene, PI5P4Kβ gene, or PI5P4Kγ gene. In other embodiments, the patient is selected for the treatment based on tumor expression of p53 mutations.

In some embodiments, administration of a compound of Formula (I) or a pharmaceutical composition comprising a compound of the present invention and a pharmaceutically acceptable carrier induces a change in the cell cycle or cell viability.

Another aspect of the invention is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of PI5P4K including, cancer or cell proliferative disorder, a metabolic disorder, neurodegenerative disease, and an inflammatory disease, comprising administering to a patient suffering from at least one of said diseases or disorder a compound of Formula (I).

One therapeutic use of the compounds or compositions of the present invention which inhibit PI5P4K is to provide treatment to patients or subjects suffering from c cancer or cell proliferative disorder, a metabolic disorder, neurodegenerative disease, and an inflammatory disease.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, pentaneG400, pentaneG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, poly(hydroxypropyl) methacrylamide-phenol, poly(hydroxyethyl)aspanamide phenol, or poly(ethyleneoxide)-polylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. All solvents used were of analytical grade and commercially available anhydrous solvents were routinely used for reactions. Starting materials were available from commercial sources, or prepared according to literature procedures. Room temperature refers to +20-25° C. Solvent mixture compositions are given as volume percentages or volume ratios.

Microwave heating was performed in a Biotage Initiator microwave cavity producing continuous irradiation at 2.45 GHz. It is understood that microwaves may be used for the heating of reaction mixtures.

Straight phase chromatography was manually performed on Merck Silica gel 60 (0.040-0.063 mm), or automatically using an ISCO Combiflash® Companion™ system using SiliaSep™ normal-phase flash columns using the solvent system indicated.

NMR spectra were recorded on a 400 MHz (or higher field) NMR spectrometer fitted with a probe of suitable configuration. Spectra were recorded at ambient temperature unless otherwise stated. Chemical shifts are given in ppm down- and upfield from TMS (0.00 ppm). The following reference signals were used: the residual solvent signal of DMSO-d6 δ 2.5, CDCl3 δ 7.26 or Methanol-d4 δ 3.31. Resonance multiplicities are denoted s, d, t, q, m and br for singlet, doublet, triplet, quartet, multiplet and broad, respectively.

High pressure liquid chromatography (HPLC) was performed on a reverse phase column. A linear gradient was applied using for example mobile phase A (aqueous 0.1% NH3 or aqueous 0.1% acetic acid or aqueous 0.1% formic acid) and B (acetonitrile or methanol). Mass spectrometer (MS) analyses were performed in positive ion mode using electrospray ionization (ES+).

Preparative chromatography was run on a Gilson-PREP GX271 or GX281 with Trilution 1c as software on a reverse phase column. A linear gradient was applied using for example mobile phase A (aqueous 0.1% NH3 or aqueous 0.1% acetic acid or aqueous 0.1% formic acid) and B (acetonitrile or methanol).

Preparative chiral chromatography for separation of enantiomers was run on a Thar SFC using supercritical fluid chromatography on a chiral stationary phase. A linear gradient was applied using mobile phase A (carbon dioxide) and B (acetonitrile or methanol or ethanol or 2-propanol or any mixtures thereof). Additives (such as diethyl amine or isopropyl amine or ammonia or formic acid or TFA) may be used.

Abbreviations used in the following examples and elsewhere herein are:
Ac$_2$O acetic anhydride
AcOH acetic acid
ADP adenosine diphosphate
Amphos (4-(N,N-dimethylamino)phenyl)di-tert-butyl phosphine
anh. anhydrous
aq. Aqueous
atm atmosphere
ATP adenosine triphosphate
B$_2$Pin$_2$ bis(pinacolato)diboron
BH$_3$·THF borane tetrahydrofuran
BINAP (±)-2,2'-bis(diphenylphosphino)-1,1'-binaphthalene
Boc tert-butyloxycarbonyl
Boc$_2$O tert-butyloxycarbonyl anhydride
Brettphos 2-(dicyclohexylphosphino)3,6-dimethoxy-2',4',6'-triisopropyl-1,1'-biphenyl
Brettphos Pd G3 [(2-di-cyclohexylphosphino-3,6-dimethoxy-2',4',6'-triisopropyl-1,1'-biphenyl)-2-(2'-amino-1,1'-biphenyl)]palladium(II) methanesulfonate
br broad
brine saturated aqueous sodium chloride
n-BuLi n-butyl lithium
n-BuOH n-butanol
Calc'd calculated
CDCl$_3$ deuterated chloroform
CHCl$_3$ chloroform
CoCl$_2$·6H$_2$O cobalt chloride hexahydrate
Cs$_2$CO$_3$ cesium carbonate
CuI copper iodide
DCM dichloromethane
DIAD diisopropyl azodiformate
DIPEA N,N-diisopropylethylamine
DMAc N,N-dimethyl acetamide
DMAP N,N-dimethylpyridin-4-amine
DME 1,2-Dimethoxyethane
DMEDA N,N'-Dimethylethylenediamine DMF N,N-dimethyl formamide
DMFDMA N,N-dimethyl formamide dimethyl acetal
2,2-DMP dimethoxypropane
DMSO dimethyl sulfoxide
DMSO-$d_6$ deuterated dimethyl sulfoxide
DOPE 1,2-dioleoyl-sn-glycero-3-phosphoethanolamine
EDA ethylenediamine
EDC 1-ethyl-3-(3-dimethylaminopropyl)carbodiimide
EDCI 1-ethyl-3-(3-dimethylaminopropyl)carbodiimide
EDTA ethylenediaminetetraacetic acid
EGTA ethylene glycol-bis(β-aminoethyl ether)-N,N,N'N'-tetraacetic acid
ESI electrospray ionization
$Et_2O$ diethyl ether
EtOAc ethyl acetateEtOH ethanol
FA formic acid
Fe iron
g gram
GST glutathione S-transferase
h hour(s)
$H_2$ hydrogen gas
$H_2O_2$ hydrogen peroxide
HATU [bis(dimethylamino)methylene]-1H-1,2,3-triazolo[4,5-b]pyridinium 3-oxide hexafluorophosphate
HBTU 3-[bis(dimethylamino)methylene]-3H-benzotriazol-1-oxide hexafluorophosphate
HBr hydrobromic acid
HCl hydrochloric acid
HEPES (4-(2-hydroxyethyl)-1-piperazineethanesulfonic acid)
HNE 20 mM HEPES, pH 7.4, 100 mM NaCl, 0.5 mM EGTA
HPLC high pressure (or performance) liquid chromatography
Hz hertz
IPA isopropanol
J coupling constant
$K_2CO_3$ potassium carbonate
$KMnO_4$ potassium permanganate
KOAc potassium acetate
KOtBu potassium tert-butoxide
LCMS liquid chromatography mass spectrometry
LHMDS lithium bis(trimethylsilyl)amide
LiOH lithium hydroxide
m multiplet
m/z mass-to-charge ratio
MBTE methyl tert-butyl ether
MeCN acetonitrile
MeI methyl iodideMeNH$_2$ methylamine
Me$_2$NH dimethylamine
MeOH methanol
Methanol-$D_4$ deuterated methanol
2-MeTHF 2-methyl tetrahydrofuran
mg milligram
$MgCl_2$ magnesium chloride
$MgSO_4$ magnesium sulfate
MHz megahertz
min min
mM millimolar
mmol millimole
mL milliliter
MOPS 3-(N-morpholino)propanesulfonic acid
MS mass spectrometry
MS ES mass spectrometry electrospray
MsCl methanesulfonyl chloride
Ms$_2$O methanesulfonic anhydride
MTBE methyl tert-butyl ether m/z mass-to-charge ratio
μg microgram
μM micromolar
μL microliter
$N_2$ nitrogen
$NaBH_4$ sodium borohydride
NaCl sodium chloride
$Na_2CO_3$ sodium carbonate
NaH sodium hydride
$NaHCO_3$ sodium bicarbonate
NaOtBu sodium tert-butoxide
$Na_2SO_4$ sodium sulfate
NaOH sodium hydroxide
$NH_3$ ammonia
$NH_4Cl$ ammonium chloride
$NH_4HCO_3$ ammonium bicarbonate
NMR nuclear magnetic resonance
Pd/C palladium on carbon
$PdCl_2$(Amphos) bis(di-tert-butyl(4-dimethylaminophenyl)phosphine)dichloropalladium(II)
$PdCl_2(PPh_3)_2$ bis(triphenylphosphinepalladium(II) dichloride
$Pd_2(dba)_3$ tris(dibenzylideneacetone)dipalladium(0)
$Pd(OAc)_2$ palladium(II) acetate
$PdCl_2$(dppf) [1,1'-bis(diphenylphosphino)ferrocene]dichloropalladium(II)
$Pd(t-Bu_3P)_2$ bis(tri-tert-butylphosphine)palladium(0)
$Pd(PPh_3)_4$ tetrakis(triphenylphosphine)palladium(0)
PEPPSI-iPr [1,3-bis(2,6-Diisopropylphenyl)imidazol-2-ylidene](3-chloropyridyl)palladium(II) dichloride
pH potential of hydrogen
PI5P phosphatidylinositol 5-phosphate
PI5P4K phosphatidylinositol-5-phosphate-4-kinase
PIP4K2A phsosphatidylinositol 5-phosphate 4-kinase type-2 alpha
ppm parts per million
psi pounds per square inch
py pyridine
quant. quantitative
$R_f$ retention factor
rt room temperature
Rt retention time
sat. saturated
SEMCl 2-(trimethylsilyl)ethoxymethyl chloride
$SOCl_2$ thionyl chloride
t-BuOH tert-butanol
TBAB tetrabutylammonium bromide
TEA triethylamine
TFA trifluoroacetic acid
THF tetrahydrofuran
TLC thin layer chromatography
TMEDA tetramethylethylenediamine
Triton X-100 4-(1,1,3,3-tetramethylbutyl)phenyl-polyethylene glycol
Ts$_2$O tosylic anhydride
TsOH tosylic acid
Tween 20 PEG(20) sorbitan monolaurate
XantPhos 4,5-bis(diphenylphosphino)-9,9-dimethylxanthene
XPhos 2-dicyclohexylphosphino-2',4',6'-triisopropylbiphenyl
XPhos Pd G1 (2-Dicyclohexylphosphino-2',4',6'-triisopropyl-1,1'-biphenyl)[2-(2-aminoethyl)phenyl)]palladium(II) chloride, (XPhos) palladium(II) phenethylamine chloride
Zn zinc Example 1: Compound 14: N-{5-[2-(3,3-difluoro-pyrrolidin-1-yl)ethoxy]pyridin-3-yl}-4-methoxy-5-[4-(4-methylpyridazin-3-yl)phenyl]pyrimidin-2-amine
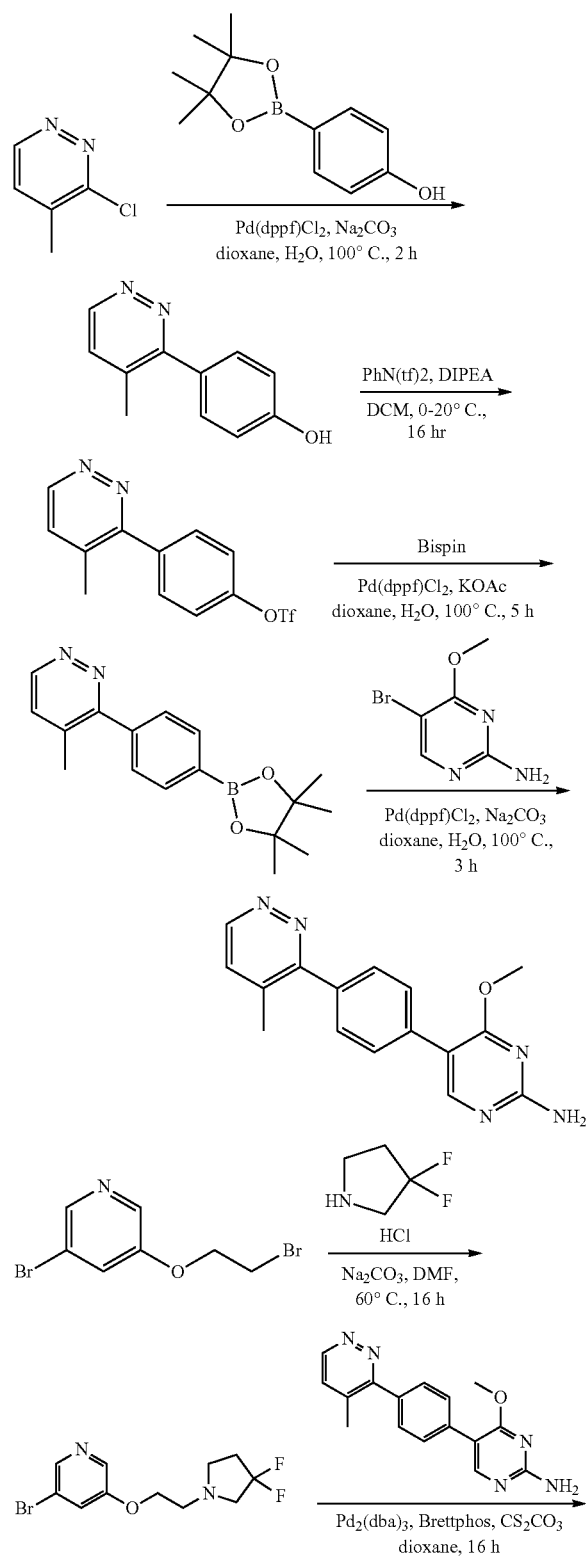
Example 2: Compound 8: (6S)-12-({5-[4-(4-methyl-4H-1,2,4-triazol-3-yl)phenyl]-4-(prop-1-en-2-yl)pyridin-2-yl}amino)-8-oxa-2,10-diazatricyclo[7.4.0.0$^{2,6}$,]trideca-1(13),9,11-trien-3-one
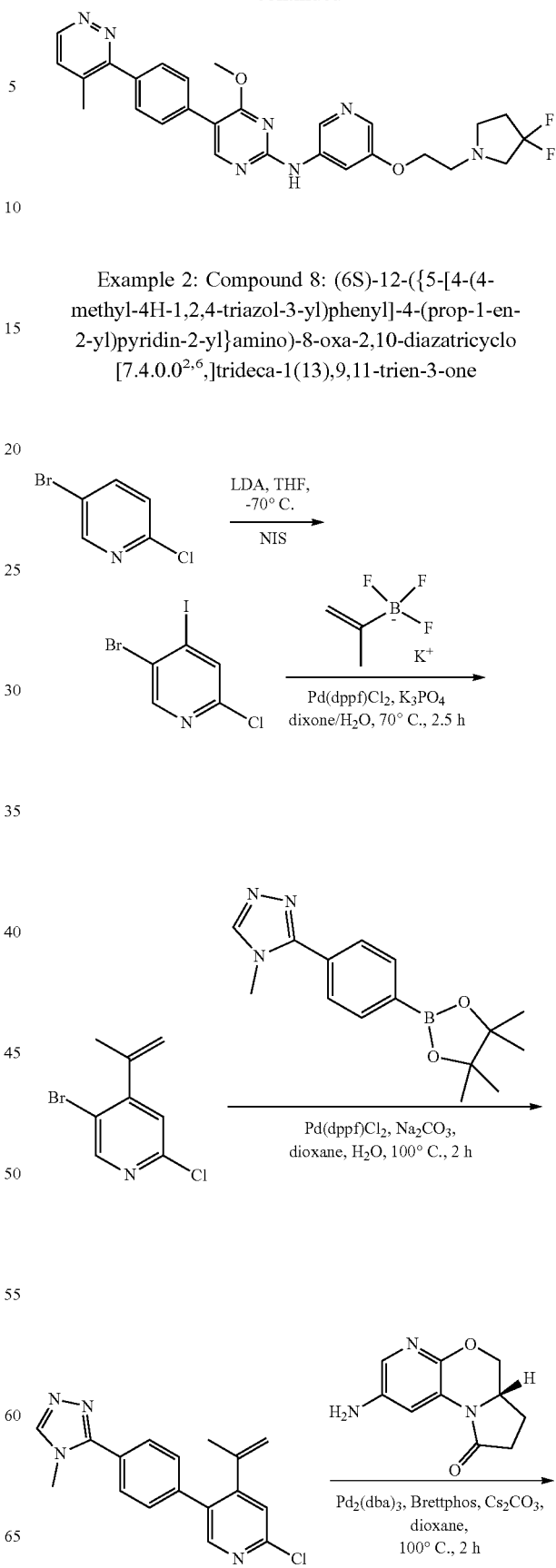

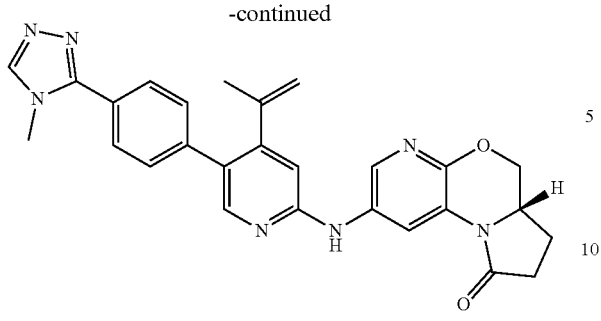

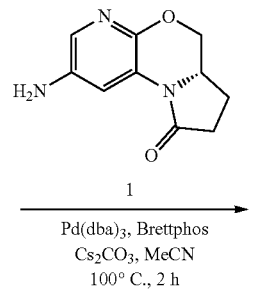

Example 3: Compound 14: (6S)-12-({5-[4-(2-oxopyrrolidin-1-yl)phenyl]-4-(trifluoromethyl)pyrimidin-2-yl}amino)-8-oxa-2,10-diazatricyclo[7.4.0.0²,⁶]trideca-1(9),10,12-trien-3-one

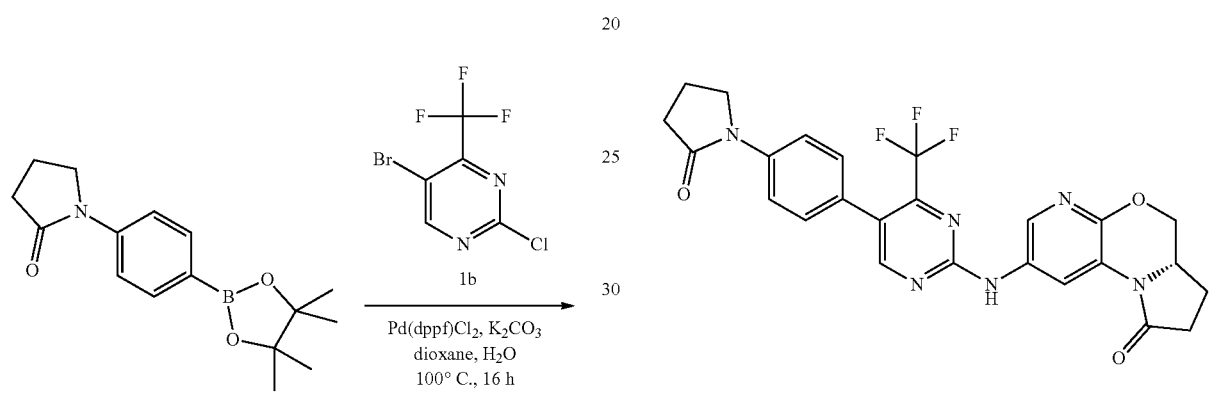

| Compound No. | Structure | Compound Name |
|---|---|---|
| 1 | 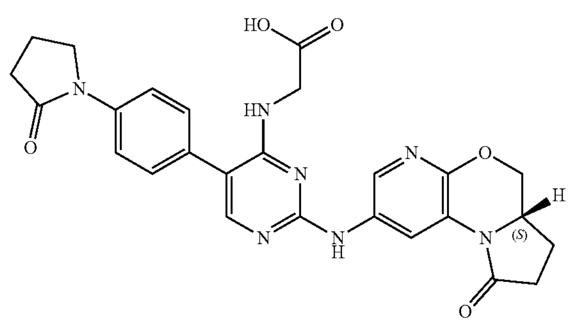 | 2-[(2-{[(6S)-3-oxo-8-oxa-2,10-diazatricyclo[7.4.0.0²,⁶]trideca-1(9),10,12-trien-12-yl]amino}-5-[4-(2-oxopyrrolidin-1-yl)phenyl]pyrimidin-4-yl)amino]acetic acid |
| 2 | 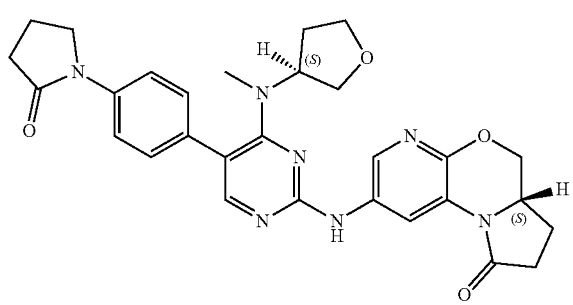 | (6S)-12-[(4-{methyl[(3S)-oxolan-3-yl]amino}-5-[4-(2-oxopyrrolidin-1-yl)phenyl]pyrimidin-2-yl)amino]-8-oxa-2,10-diazatricyclo[7.4.0.0²,⁶]trideca-1(13),9,11-trien-3-one |

-continued

| Compound No. | Structure | Compound Name |
|---|---|---|
| 3 | 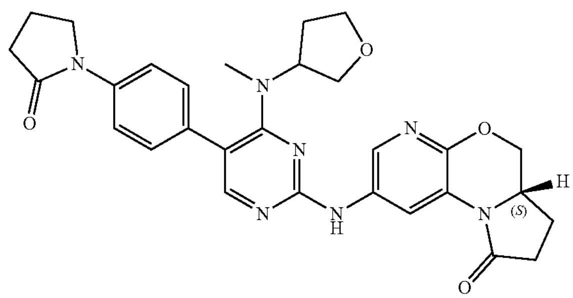 | (6S)-12-({4-[methyl(oxolan-3-yl)amino]-5-[4-(2-oxopyrrolidin-1-yl)phenyl]pyrimidin-2-yl}amino)-8-oxa-2,10-diazatricyclo[7.4.0.0²,⁶]trideca-1(13),9,11-trien-3-one |
| 4 | 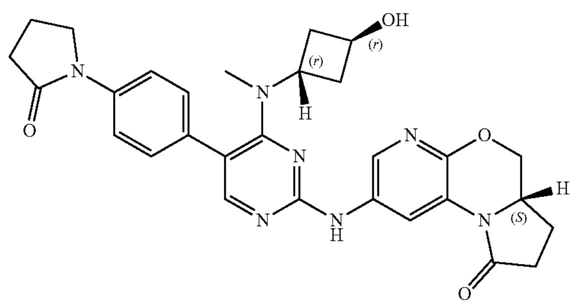 | (6S)-12-[(4-{methyl[(1r,3r)-3-hydroxycyclobutyl]amino}-5-[4-(2-oxopyrrolidin-1-yl)phenyl]pyrimidin-2-yl)amino]-8-oxa-2,10-diazatricyclo[7.4.0.0²,⁶]trideca-1(13),9,11-trien-3-one |
| 5 | 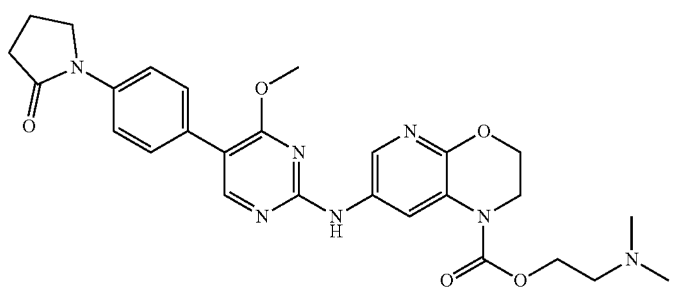 [SMILES: COc1nc(Nc2cnc3c(c2)N(C(=O)OCCN(C)C)CCO3)ncc1-c1ccc(N2CCCC2=O)cc1] | 2-(dimethylamino)ethyl 7-({4-methoxy-5-[4-(2-oxopyrrolidin-1-yl)phenyl]pyrimidin-2-yl}amino)-1H,2H,3H-pyrido[2,3-b][1,4]oxazine-1-carboxylate |
| 6 | 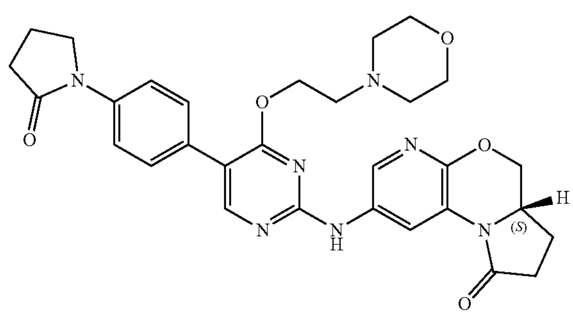 | (6S)-12-({4-[2-(morpholin-4-yl)ethoxy]-5-[4-(2-oxopyrrolidin-1-yl)phenyl]pyrimidin-2-yl}amino)-8-oxa-2,10-diazatricyclo[7.4.0.0²,⁶]trideca-1(9),10,12-trien-3-one |
| 7 | 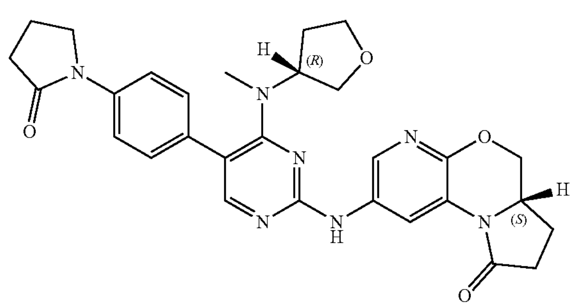 | (6S)-12-[(4-{methyl[(3R)-oxolan-3-yl]amino}-5-[4-(2-oxopyrrolidin-1-yl)phenyl]pyrimidin-2-yl)amino]-8-oxa-2,10-diazatricyclo[7.4.0.0²,⁶]trideca-1(13),9,11-trien-3-one |

-continued

| Compound No. | Structure | Compound Name |
|---|---|---|
| 8 | 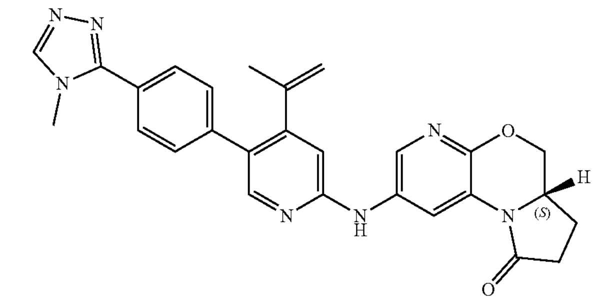 | (6S)-12-({5-[4-(4-methyl-4H-1,2,4-triazol-3-yl)phenyl]-4-(prop-1-en-2-yl)pyridin-2-yl}amino)-8-oxa-2,10-diazatricyclo[7.4.0.0²,⁶]trideca-1(13),9,11-trien-3-one |
| 9 | 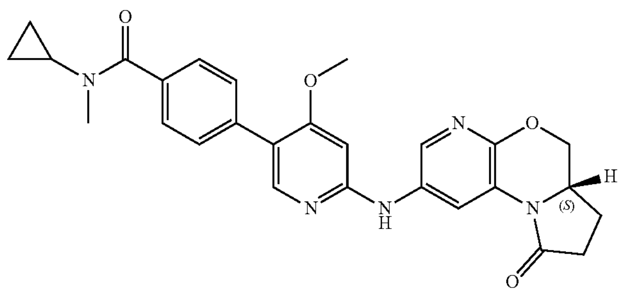 | N-cyclopropyl-4-(4-methoxy-2-{[(6S)-3-oxo-8-oxa-2,10-diazatricyclo[7.4.0.0²,⁶]trideca-1(9),10,12-trien-12-yl]amino}pyrimidin-5-yl)-N-methylbenzamide |
| 10 | 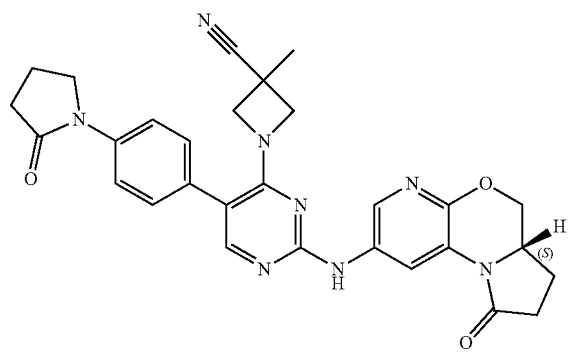 | 3-methyl-1-(2-{[(6S)-3-oxo-8-oxa-2,10-diazatricyclo[7.4.0.0²,⁶]trideca-1(13),9,11-trien-12-yl]amino}-5-[4-(2-oxopyrrolidin-1-yl)phenyl]pyrimidin-4-yl)azetidine-3-carbonitrile |
| 11 | 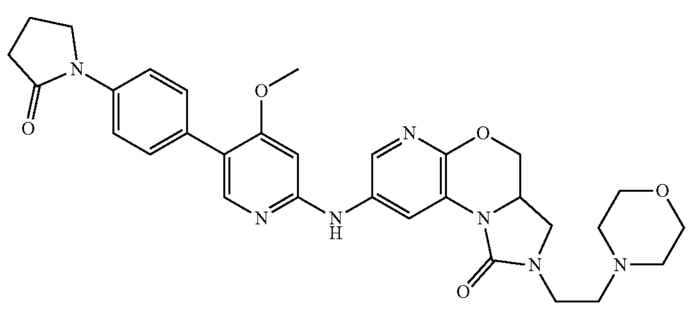 [SMILES: COc1cc(Nc2cnc3c(c2)N2C(=O)N(CCN4CCOCC4)CC2CO3)ncc1-c1ccc(N2CCCC2=O)cc1] | 12-({4-methoxy-5-[4-(2-oxopyrrolidin-1-yl)phenyl]pyrimidin-2-yl}amino)-4-[2-(morpholin-4-yl)ethyl]-8-oxa-2,4,10-triazatricyclo[7.4.0.0²,⁶]trideca-1(9),10,12-trien-3-one |
| 12 | 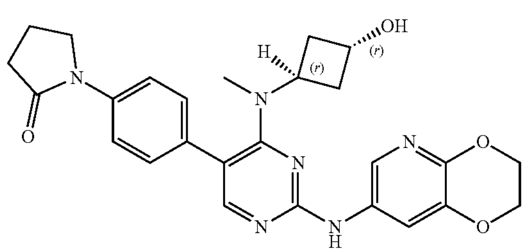 | 1-{4-[2-({2H,3H-[1,4]dioxino[2,3-b]pyridin-7-yl}amino)-4-{methyl[(1r,3r)-3-hydroxycyclobutyl]amino}pyrimidin-5-yl]phenyl}pyrrolidin-2-one |

-continued

| Compound No. | Structure | Compound Name |
|---|---|---|
| 13 | 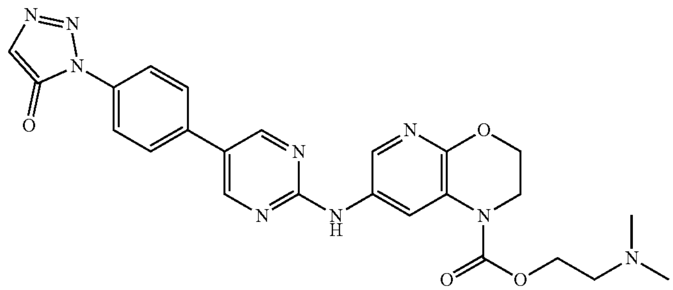 | 2-(dimethylamino)ethyl 7-({5-[4-(5-methyl-1H-1,2,3-triazol-1-yl)phenyl]pyrimidin-2-yl}amino)-1H,2H,3H-pyrido[2,3-b][1,4]oxazine-1-carboxylate |
| 14 | 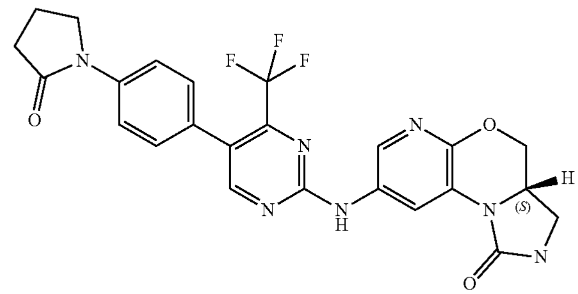 | (6S)-12-({5-[4-(2-oxopyrrolidin-1-yl)phenyl]-4-(trifluoromethyl)pyrimidin-2-yl}amino)-8-oxa-2,10-diazatricyclo[7.4.0.0²,⁶]trideca-1(9),10,12-trien-3-one |
| 15 | 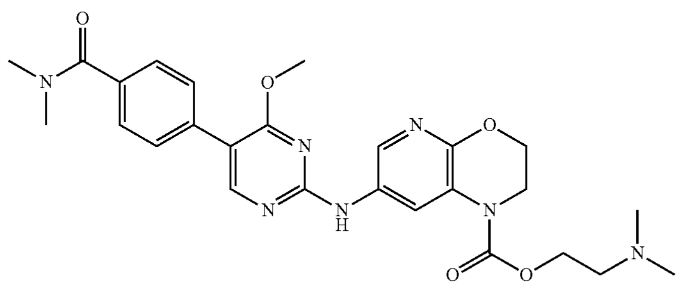 | 2-(dimethylamino)ethyl 7-({5-[4-(dimethylcarbamoyl)phenyl]-4-methoxypyrimidin-2-yl}amino)-1H,2H,3H-pyrido[2,3-b][1,4]oxazine-1-carboxylate |
| 16 | 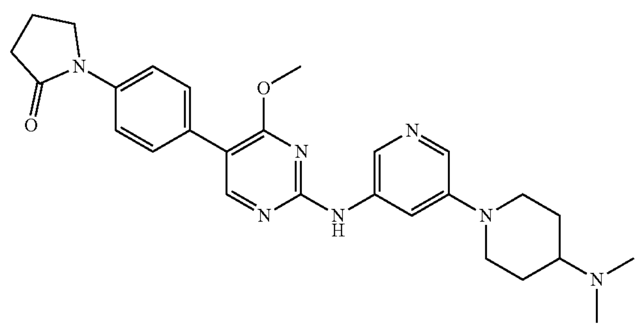 [SMILES: COc1nc(Nc2cncc(N3CCC(N(C)C)CC3)c2)ncc1-c1ccc(N2CCCC2=O)cc1] | 1-{4-[2-({5-[4-(dimethylamino)piperidin-1-yl]pyridin-3-yl}amino)-4-methoxypyrimidin-5-yl]phenyl}pyrrolidin-2-one |
| 17 | 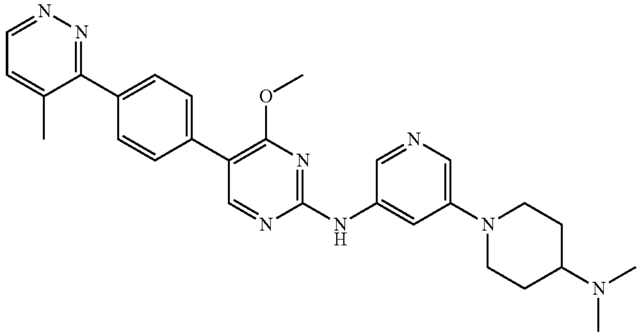 [SMILES: COc1nc(Nc2cncc(N3CCC(N(C)C)CC3)c2)ncc1-c1ccc(-c2nnccc2C)cc1] | N-{5-[4-(dimethylamino)piperidin-1-yl]pyridin-3-yl}-4-methoxy-5-[4-(4-methylpyridazin-3-yl)phenyl]pyrimidin-2-amine |

-continued

| Compound No. | Structure | Compound Name |
|---|---|---|
| 18 | 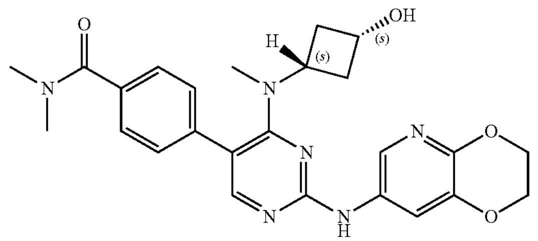 | 4-[2-({2H,3H-[1,4]dioxino[2,3-b]pyridin-7-yl}amino)-4-{methyl[(1s,3s)-3-hydroxycyclobutyl]amino}pyrimidin-5-yl]-N,N-dimethylbenzamide |
| 19 | 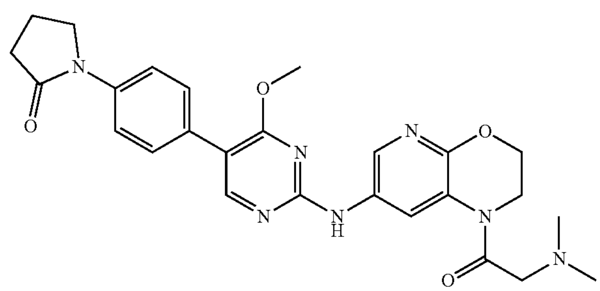 [SMILES: COc1nc(Nc2cnc3c(c2)N(C(=O)CN(C)C)CCO3)ncc1-c1ccc(N2CCCC2=O)cc1] | 1-{4-[2-({1-[2-(dimethylamino)acetyl]-1H,2H,3H-pyrido[2,3-b][1,4]oxazin-7-yl}amino)-4-methoxypyrimidin-5-yl]phenyl}pyrrolidin-2-one |
| 20 | 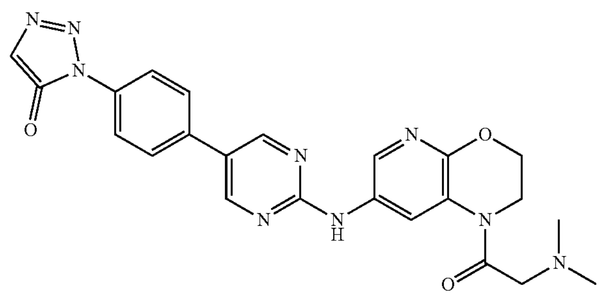 | 2-(dimethylamino)-1-[7-({5-[4-(5-methyl-1H-1,2,3-triazol-1-yl)phenyl]pyrimidin-2-yl}amino)-1H,2H,3H-pyrido[2,3-b][1,4]oxazin-1-yl]ethan-1-one |
| 21 | 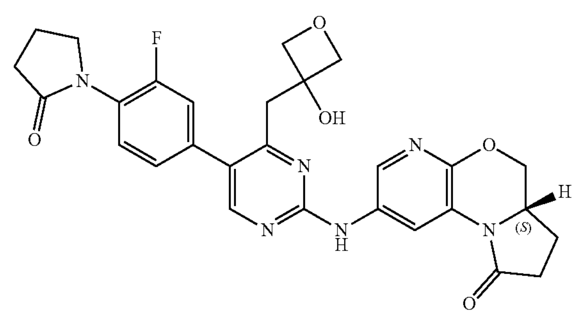 | (6S)-12-({5-[3-fluoro-4-(2-oxopyrrolidin-1-yl)phenyl]-4-[(3-hydroxyoxetan-3-yl)methyl]pyrimidin-2-yl}amino)-8-oxa-2,10-diazatricyclo[7.4.0.0$^{2,6}$]trideca-1(9),10,12-trien-3-one |
| 22 | 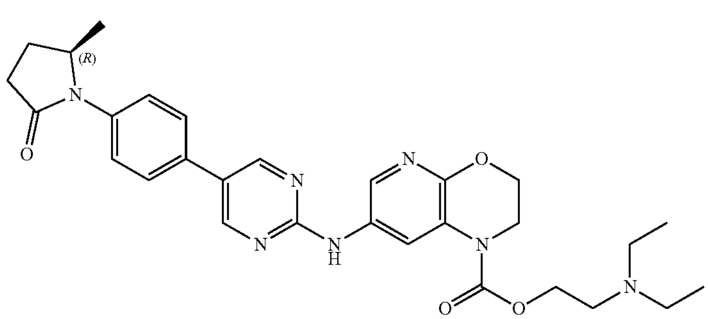 | 2-(diethylamino)ethyl 7-[(5-{4-[(2R)-2-methyl-5-oxopyrrolidin-1-yl]phenyl}pyrimidin-2-yl)amino]-1H,2H,3H-pyrido[2,3-b][1,4]oxazine-1-carboxylate |

| Compound No. | Structure | Compound Name |
|---|---|---|
| 23 | 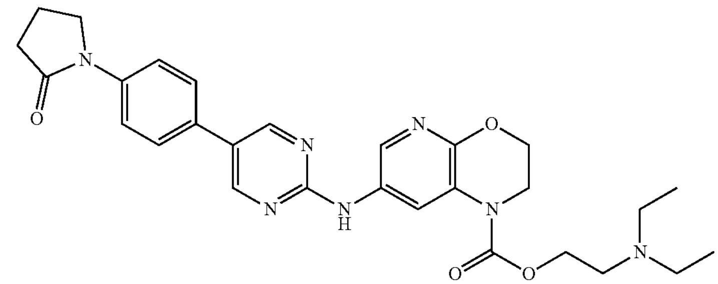 [SMILES: CCN(CC)CCOC(=O)N1CCOc2ncc(Nc3ncc(-c4ccc(N5CCCC5=O)cc4)cn3)cc21] | 2-(diethylamino)ethyl 7-({5-[4-(2-oxopyrrolidin-1-yl)phenyl]pyrimidin-2-yl}amino)-1H,2H,3H-pyrido[2,3-b][1,4]oxazine-1-carboxylate |
| 24 | 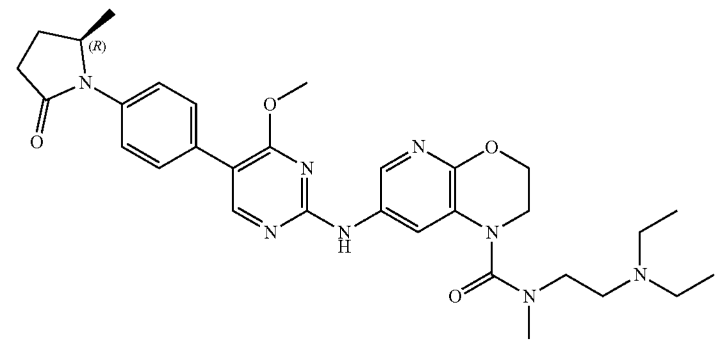 | N-[2-(diethylamino)ethyl]-7-[(4-methoxy-5-{4-[(2R)-2-methyl-5-oxopyrrolidin-1-yl][phenyl}pyrimidin-2-yl)amino]-N-methyl-1H,2H,3H-pyrido[2,3-b][1,4]oxazine-1-carboxamide |
| 25 | 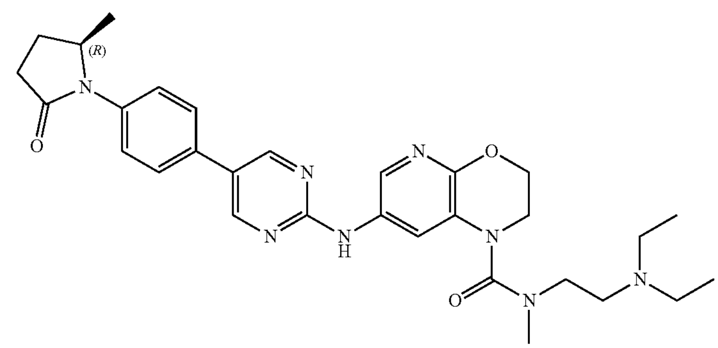 | N-[2-(diethylamino)ethyl]-N-methyl-7-[(5-{4-[(2R)-2-methyl-5-oxopyrrolidin-1-yl]phenyl}pyrimidin-2-yl)amino]-1H,2H,3H-pyrido[2,3-b][1,4]oxazine-1-carboxamide |
| 26 | 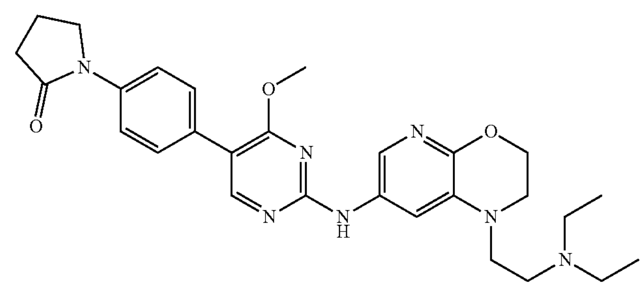 [SMILES: CCN(CC)CCN1CCOc2ncc(Nc3ncc(-c4ccc(N5CCCC5=O)cc4)c(OC)n3)cc21] | 1-{4-[2-({1-[2-(diethylamino)ethyl]-1H,2H,3H-pyrido[2,3-b][1,4]oxazin-7-yl}amino)-4-methoxypyrimidin-5-yl]phenyl}pyrrolidin-2-one |
| 27 | 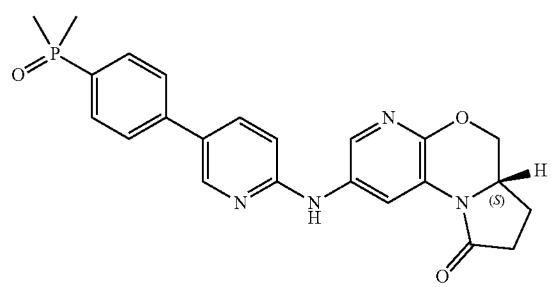 | (6S)-12-({5-[4-(dimethylphosphoryl)phenyl]pyridin-2-yl}amino)-8-oxa-2,10-diazatricyclo[7.4.0.0²,⁶]trideca-1(9),10,12-trien-3-one |

-continued

| Compound No. | Structure | Compound Name |
|---|---|---|
| 28 | 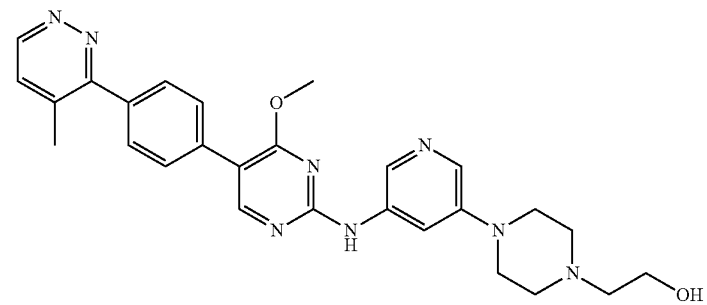 [SMILES: COc1nc(Nc2cncc(N3CCN(CCO)CC3)c2)ncc1-c1ccc(-c2nnccc2C)cc1] | 2-{4-[5-({4-methoxy-5-[4-(4-methylpyridazin-3-yl)phenyl]pyrimidin-2-yl}amino)pyridin-3-yl]piperazin-1-yl}ethan-1-ol |
| 29 | 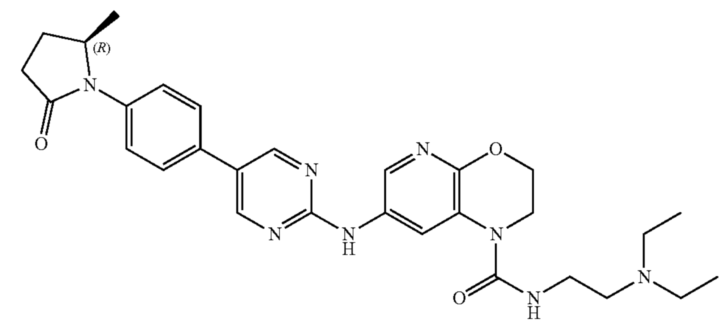 | N-[2-(diethylamino)ethyl]-7-[(5-{4-[(2R)-2-methyl-5-oxopyrrolidin-1-yl]phenyl}pyrimidin-2-yl)amino]-1H,2H,3H-pyrido[2,3-b][1,4]oxazine-1-carboxamide |
| 30 | 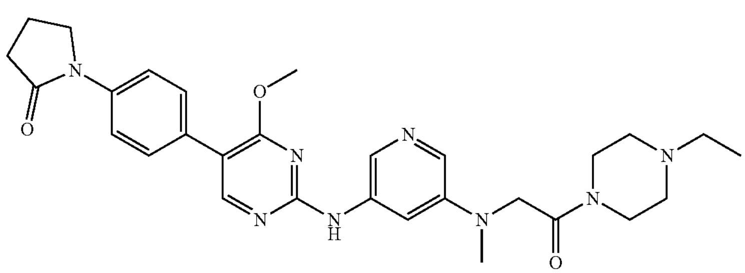 [SMILES: CCN1CCN(C(=O)CN(C)c2cncc(Nc3ncc(-c4ccc(N5CCCC5=O)cc4)c(OC)n3)c2)CC1] | 1-(4-{2-[(5-{[2-(4-ethylpiperazin-1-yl)-2-oxoethyl](methyl)amino}pyridin-3-yl)amino]-4-methoxypyrimidin-5-yl}phenyl)pyrrolidin-2-one |
| 31 | 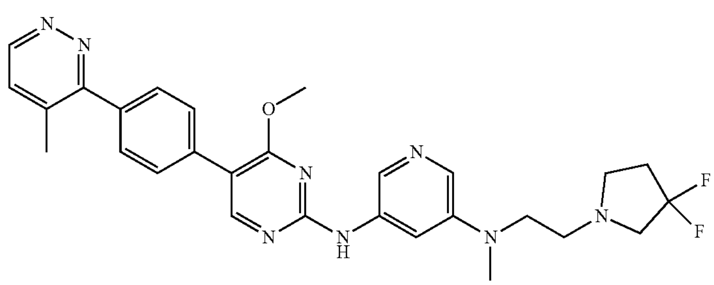 [SMILES: COc1nc(Nc2cncc(N(C)CCN3CCC(F)(F)C3)c2)ncc1-c1ccc(-c2nnccc2C)cc1] | N3-[2-(3,3-difluoropyrrolidin-1-yl)ethyl]-N5-{4-methoxy-5-[4-(4-methylpyridazin-3-yl)phenyl]pyrimidin-2-yl}-N3-methylpyridine-3,5-diamine |
| 32 | 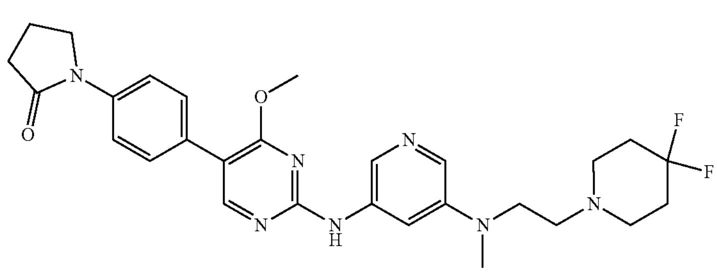 [SMILES: COc1nc(Nc2cncc(N(C)CCN3CCC(F)(F)CC3)c2)ncc1-c1ccc(N2CCCC2=O)cc1] | 1-(4-{2-[(5-{[2-(4,4-difluoropiperidin-1-yl)ethyl](methyl)amino}pyridin-3-yl)amino]-4-methoxypyrimidin-5-yl}phenyl)pyrrolidin-2-one |

| Compound No. | Structure | Compound Name |
|---|---|---|
| 33 | 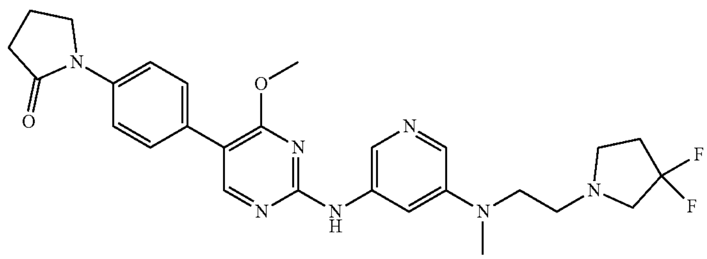 [SMILES: COc1nc(Nc2cncc(N(C)CCN3CCC(F)(F)C3)c2)ncc1-c1ccc(N2CCCC2=O)cc1] | 1-(4-{2-[(5-{[2-(3,3-difluoropyrrolidin-1-yl)ethyl](methyl)amino}pyridin-3-yl)amino]-4-methoxypyrimidin-5-yl}phenyl)pyrrolidin-2-one |
| 34 | 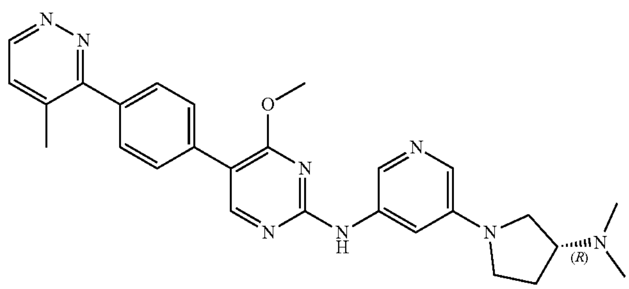 | N-{5-[(3R)-3-(dimethylamino)pyrrolidin-1-yl]pyridin-3-yl}-4-methoxy-5-[4-(4-methylpyridazin-3-yl)phenyl]pyrimidin-2-amine |
| 35 | 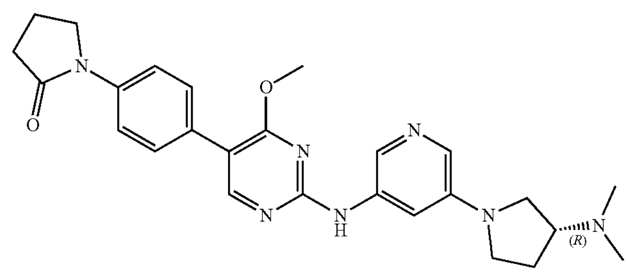 | 1-{4-[2-({5-[(3R)-3-(dimethylamino)pyrrolidin-1-yl]pyridin-3-yl}amino)-4-methoxypyrimidin-5-yl]phenyl}pyrrolidin-2-one |
| 36 | 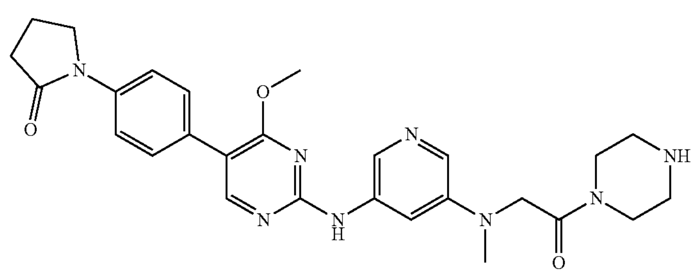 [SMILES: COc1nc(Nc2cncc(N(C)CC(=O)N3CCNCC3)c2)ncc1-c1ccc(N2CCCC2=O)cc1] | 1-(4-{4-methoxy-2-[(5-{methyl[2-oxo-2-(piperazin-1-yl)ethyl]amino}pyridin-3-yl)amino]pyrimidin-5-yl}phenyl)pyrrolidin-2-one |
| 37 | 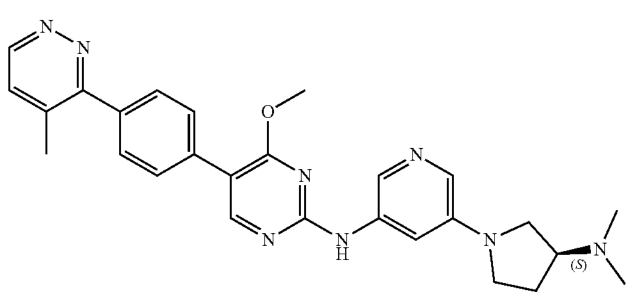 | N-{5-[(3S)-3-(dimethylamino)pyrrolidin-1-yl]pyridin-3-yl}-4-methoxy-5-[4-(4-methylpyridazin-3-yl)phenyl]pyrimidin-2-amine |

| Compound No. | Structure | Compound Name |
|---|---|---|
| 38 | 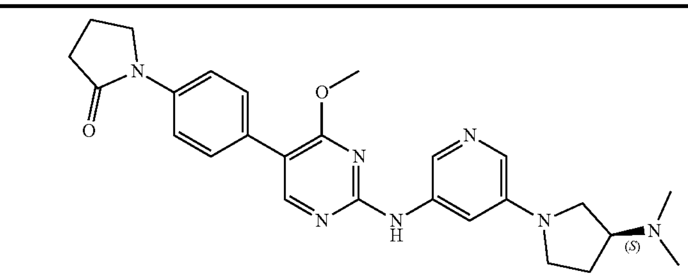 | 1-{4-[2-({5-[(3S)-3-(dimethylamino)pyrrolidin-1-yl]pyridin-3-yl}amino)-4-methoxypyrimidin-5-yl]phenyl}pyrrolidin-2-one |
| 39 | 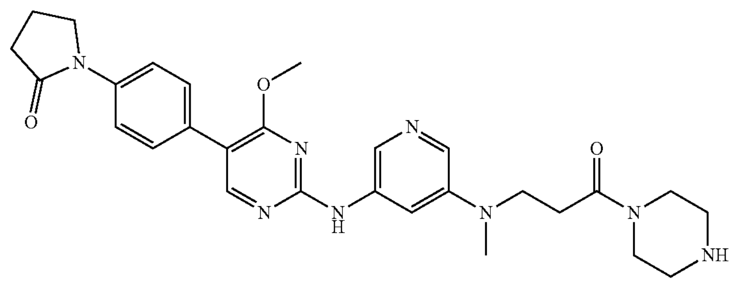 [SMILES: COc1nc(Nc2cncc(N(C)CCC(=O)N3CCNCC3)c2)ncc1-c1ccc(N2CCCC2=O)cc1] | 1-(4-{4-methoxy-2-[(5-{methyl[3-oxo-3-(piperazin-1-yl)propyl]amino}pyridin-3-yl)amino]pyrimidin-5-yl}phenyl)pyrrolidin-2-one |
| 40 | 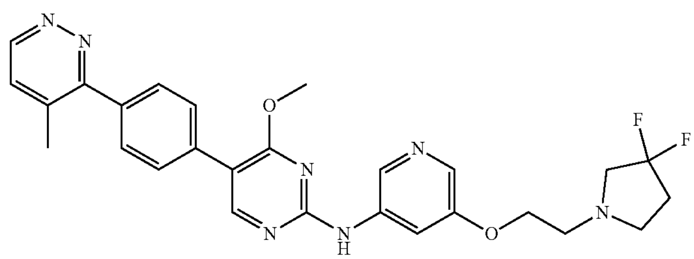 [SMILES: COc1nc(Nc2cncc(OCCN3CCC(F)(F)C3)c2)ncc1-c1ccc(-c2nnccc2C)cc1] | N-{5-[2-(3,3-difluoropyrrolidin-1-yl)ethoxy]pyridin-3-yl}-4-methoxy-5-[4-(4-methylpyridazin-3-yl)phenyl]pyrimidin-2-amine |
| 41 | 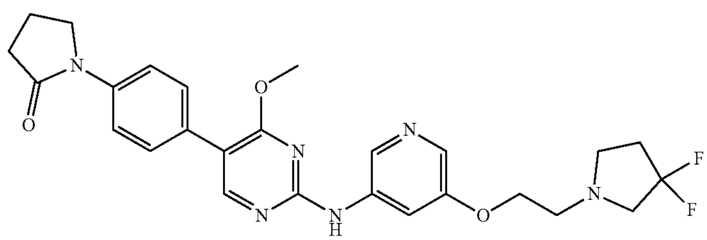 [SMILES: COc1nc(Nc2cncc(OCCN3CCC(F)(F)C3)c2)ncc1-c1ccc(N2CCCC2=O)cc1] | 1-{4-[2-({5-[2-(3,3-difluoropyrrolidin-1-yl)ethoxy]pyridin-3-yl}amino)-4-methoxypyrimidin-5-yl]phenyl}pyrrolidin-2-one |

Biochemical Assays

Example 4: ADP-Glo Biochemical Assay

Dilution series of the compounds were prepared in DMSO at 100 times the final assay concentration ($n_1=n_0/3$ in 10 points). The compounds were further diluted to three times the assay concentration in assay buffer (20 mM MOPS pH 7.2, 25 mM magnesium chloride, 0.005% Tween 20). 6 μL of the diluted compounds were added to a 384 well assay plate followed by 9 μL of a mix consisting of 4 nM PIP4K2A (full length protein, SignalChem) and 100 μM PI(5)P diC8 (Tebu-Bio). Enzyme and compounds were pre-incubated at room temperature for 15 minutes.

Then 3 μL of a solution containing 60 μM ATP (Promega) in assay buffer was added to the wells containing compound and enzyme and mixing was performed by pipetting several times. The reaction was incubated at room temperature for 1 h. Then 18 μL of ADP-Glo™ Reagent (Promega) was added to stop the kinase reaction and deplete the unconsumed ATP, mixing was performed by pipetting several times. The plate was incubated at room temperature for 40 minutes before addition of 36 μL of Kinase Detection Reagent (Promega) to convert ADP to ATP and introduce luciferase and luciferin to detect ATP. The reaction was incubated at room temperature for 40 minutes before the luminescence was measured in a in a Victor 3V 1420 multilabel counter (Perkin Elmer).

Percent inhibition of the compounds as compared to dimethyl sulfoxide treated control samples was calculated. Compound concentration versus percent inhibition were fitted to generate $IC_{50}$ values.

Example 5: Assay Protocol-PIP4KtypeIIA

GST tagged PIP4KtypeIIA and B enzymes were overexpressed in *E. Coli* and purified to >80% homogeneity. Phosphatidyl inositol-5-phosphate (PI5P, Cat. #850152, Avanti Polar Lipids Inc.) was used as the lipid substrate and phosphatidyl ethanolamine (DOPE 18:1, Cat. #850725, Avanti Polar Lipids Inc.) was used as the carrier lipid for assays. Ultrapure ATP and GTP was purchased from Bellbrooke Labs. ADP Glo reagents were obtained from Promega. Transcreener FI reagent was obtained from Bellbrooke labs.

Buffers:
1. HEPES buffer mix: 200 mM HEPES pH 7.4, 50 mM $MgCl_2$, 0.05% v/v triton X 100
2. HNE buffer: 20 mM HEPES, pH 7.4, 100 mM NaCl, 0.5 mM EGTA
3. H:E buffer: 30 mM HEPES, pH 7.4, 1 mM EGTA Enzyme preparation: GST-tagged PIP4KtypeIIA (5 μL, 1.43 mg/mL) was diluted (1:10) to 50 μL using HNE buffer. From the 1:10 diluted stock, a 6.4 μL aliquot was diluted further to 5 mL using HNE buffer to yield 5× enzyme stock (2.5 nM).

GST-tagged PIP4KtypeIIB (3.4 μl, 2.77 mg/mL) was diluted to 5 mL using HNE buffer to yield 5× enzyme stock (25 nM)

Lipid Preparation: In a 10 mL pyrex glass vial, 1 μg of PI5P and 1 μg of DOPE were suspended in 2.5 mL of HEPES buffer mix and 2.5 mL of H:E buffer. The contents were mixed and sonicated for 3 min to yield a translucent lipid stock.

Compound Preparation: Compounds were stored as 5 mM stocks in neat DMSO as room temperature in glass vials. 5 mM stocks were diluted to 2 mM and then serially diluted (3×) in neat DMSO in 96 well polypropylene plates. From the serially diluted stocks, 3 μL was delivered into 250 μL of 25% DMSO (in water) to generate 5× compound stocks. Typically, the highest compound conc. was 24 μM.

Example 6: PIP4KtypeIIA Inhibition Assay

The assay volume was kept at 25 μL. To each well of the reaction plate, 10 μL of lipid stock (1:1 ratio PI5P:DOPE) was delivered. This was followed by the addition of 5 μL of compound in 25% DMSO. Then, to each well, 5 μL of 2.5 nM (5×) typeIIA enzyme was delivered. The contents were mixed well and incubated for 1 h at 27° C. After 1 h, reaction was initiated by adding 5 μL of 50 μM ATP and the contents were mixed well with a multi-channel pipetteman. The final concentration of the reagents are as follows: 50 mM HEPES, pH 7.3, 10 mM $MgCl_2$, 20 mM NaCl, 0.01% v/v triton-X100, 5% DMSO, 10 μM ATP, 80 μM (2 μg) PI5P, 2 μg DOPE, and 0.5 nM PIP4KIIA. Typically, the highest conc. of compounds was 4.8 μM and the lowest conc. was 0.

After 1 h, the reaction was quenched by adding 25 μL of ADP Glo reagent. The contents were incubated for 1 h. Afterwards, 50 μL of kinase detection reagent was delivered. The contents were incubated for another hour. The luminescence was read using Molecular Devices Paradigm plate reader. Each plate had a "No inhibitor" control (max. activity, 4 wells) and a blank (background noise, 4 wells). The blanks were averaged and subtracted from all other wells. Using a calibration curve, RLU was converted to μM ADP (product). IC50 was calculated by plotting the residual activity (expressed as % No inhibitor control) vs. log [Inh. conc.]

Example 7: PIP4KtypeIIB Inhibition Assay

The assay volume was kept at 25 μL. To each well of the reaction plate, 10 μL of lipid stock (1:1 ratio PI5P:DOPE) was delivered. This was followed by the addition of 5 μL of compound in 25% DMSO. Then, to each well, 5 μL of 25 nM (5×) typeIIB enzyme was delivered. The contents were mixed well and incubated for 1 h at 27° C. After 1 h, reaction was initiated by adding 5 μL of 500 μM GTP and the contents were mixed well with a multi-channel pipetteman. The final concentration of the reagents are as follows: 50 mM HEPES, pH 7.3, 10 mM $MgCl_2$, 20 mM NaCl, 0.01% v/v triton-X100, 5% DMSO, 100 μM GTP, 80 μM (2 μg) PI5P, 2 μg DOPE, and 5 nM PIP4KIIB Typically, the highest conc. of compounds was 4.8 μM and the lowest conc. was 0.

After 2 h, the reaction was quenched by adding 25 μL of transcreener FI reagent. The contents were incubated at rt for 1 h and the Fluorescence (Ex: 584 Em: 623) was read using Molecular Devices Paradigm plate reader. Each plate had a "No inhibitor" control (max. activity, 4 wells) and a blank (background noise, 4 wells). The blanks were averaged and subtracted from all other wells. Using a calibration curve, RFU was converted to μM GDP (product). $IC_{50}$ was calculated by plotting the residual activity (expressed as % No inhibitor control) vs. log [Inh. conc.].

TABLE 2 represents PI5P4K activity of compounds of the invention arranged in accordance with the inhibition of PIP4K2 A kinase assay.

| Kinase Assay-PIP4K2 A |
| --- |
| $IC_{50} \leq 1$ nM |

| 1 |
| --- |
| 2 |
| 3 |

| Kinase Assay-PIP4K2 A |
| --- |
| $1 < IC_{50} \leq 10$ nM |

| 4 |
| --- |
| 5 |
| 6 |
| 7 |
| 8 |
| 9 |
| 10 |
| 11 |
| 12 |
| 13 |
| 14 |
| 15 |
| 36 |

| Kinase Assay-PIP4K2 A |
| --- |
| $10 < IC_{50} \leq 100$ nM |

| 16 |
| --- |
| 17 |
| 18 |
| 19 |
| 20 |
| 21 |
| 22 |
| 23 |
| 34 |
| 37 |
| 38 |
| 39 |
| 40 |
| 41 |

TABLE 2-continued represents PI5P4K activity of compounds of the invention arranged in accordance with the inhibition of PIP4K2 A kinase assay.

| Kinase Assay-PIP4K2 A $100 < IC_{50} \leq 1000$ nM |
| --- |
| 24 |
| 25 |
| 26 |
| 35 |

| Kinase Assay-PIP4K2 A $IC_{50} > 1000$ nM |
| --- |
| 27 |

TABLE 3 represents PIP4K activity of compounds of the invention arranged in accordance with the inhibition of PIP4K2 B kinase assay.

| Kinase Assay-PIP4K2 B $IC_{50} \leq 1$ nM |
| --- |
| 1 |

| Kinase Assay-PIP4K2 B $1 < IC_{50} \leq 10$ nM |
| --- |
| 2 |
| 3 |
| 4 |
| 5 |
| 6 |
| 7 |
| 8 |
| 9 |
| 10 |
| 11 |
| 12 |
| 13 |
| 14 |
| 15 |

| Kinase Assay-PIP4K2 B $10 < IC_{50} \leq 100$ nM |
| --- |
| 16 |
| 17 |
| 19 |
| 20 |
| 21 |
| 22 |
| 23 |
| 24 |
| 34 |
| 36 |
| 37 |
| 38 |
| 39 |
| 40 |
| 41 |

| Kinase Assay-PIP4K2 B $100 < IC_{50} \leq 1000$ nM |
| --- |
| 18 |
| 25 |
| 26 |
| 35 |

TABLE 3-continued represents PIP4K activity of compounds of the invention arranged in accordance with the inhibition of PIP4K2 B kinase assay.

| Kinase Assay-PIP4K2 B $IC_{50} > 1000$ nM |
| --- |
| 27 |

TABLE 4 represents PI5P4K activity of compounds of the invention arranged in accordance with the MOLM-16 $EC_{50}$ assay.

| MOLM-16 $10 < EC_{50} \leq 100$ nM |
| --- |
| 5 |
| 6 |
| 9 |
| 16 |
| 19 |
| 34 |
| 35 |
| 37 |
| 38 |
| 41 |

| MOLM-16 $100 < EC_{50} \leq 1000$ nM |
| --- |
| 10 |
| 11 |
| 12 |
| 13 |
| 15 |
| 20 |
| 26 |
| 36 |
| 39 |
| 40 |

| MOLM-16 $EC_{50} > 1000$ nM |
| --- |
| 1 |
| 2 |
| 3 |
| 4 |
| 7 |
| 8 |
| 14 |
| 18 |
| 21 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of Formula (Id):

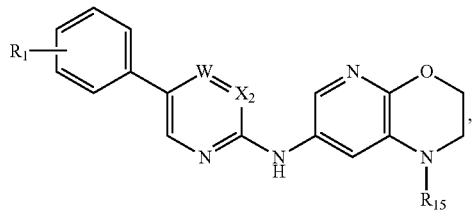

(Id)

or a pharmaceutically acceptable salt, prodrug, solvate, hydrate, stereoisomer, or tautomer thereof, wherein
$X_2$ is $C(R_5)$ or N;
W is $C(R_6)$;
$R_1$ is —$N(R_2)C(O)R_3$, —$C(O)N(R_2)(R_3)$, —$P(O)(R_2)(R_3)$, or heteroaryl, wherein the heteroaryl is optionally substituted with one or more $R_7$;
$R_2$ is $C_{1-6}$ alkyl;
$R_3$ is $C_{1-6}$ alkyl or $C_{3-8}$ cycloalkyl; or
$R_2$ and $R_3$ when taken together with the atom to which they are each attached form a heterocycle optionally substituted with one or more $R_4$;
each $R_4$ is independently —H or $C_{1-6}$ alkyl;
$R_5$ is —H;
$R_6$ is —H, —$N(R_{26})(R_{27})$, $C_{1-6}$ alkoxy, heterocyclyl, $C_{2-6}$ alkenyl, $C_{1-6}$ haloalkyl, or $C_{1-6}$ alkyl, wherein the $C_{1-6}$ alkyl, $C_{2-6}$ alkenyl, $C_{1-6}$ alkoxy, or heterocyclyl is optionally substituted with one or more —OH, —CN, $C_{1-6}$ alkyl, or heterocyclyl;
each $R_7$ is independently $C_{1-6}$ alkyl;
$R_{15}$ is —$N(C_{1-6}$ alkyl$)_2$, $C_{1-6}$ alkyl, —$C(O)N(R_{21})(R_{23})$, —$(CH_2)_o$—$C(O)R_{23}$, or —$C(O)OR_{23}$, wherein the $C_{1-6}$ alkyl is optionally substituted with one or more $R_{23}$;
$R_{21}$ is —H or $C_{1-6}$ alkyl;
each $R_{23}$ is independently $C_{1-6}$ alkyl optionally substituted with one or more —$N(C_{1-6}$ alkyl$)_2$; or
two $R_{23}$ when taken together with the atom to which they are each attached form a heterocyclyl, wherein the heterocyclyl is optionally substituted by $C_{1-6}$ alkyl;
$R_{26}$ is —H or $C_{1-6}$ alkyl;
$R_{27}$ is $C_{1-6}$ alkyl, heterocyclyl, or cycloalkyl, wherein the $C_{1-6}$ alkyl, heterocyclyl, or cycloalkyl is optionally substituted with one or more halogen, —CN, —C(O)OH, —OH, or —$NH_2$; and
o is 0-4.

2. The compound of claim 1 having the Formula (Ie):

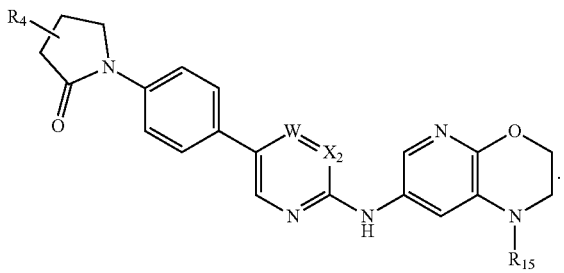

(Ie)

3. The compound of claim 1 having the Formula (If):

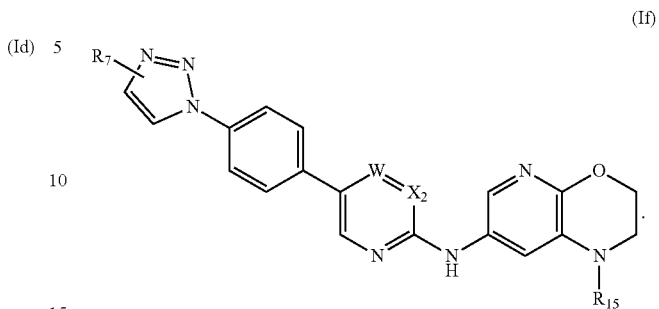

(If)

4. The compound of claim 1 selected from the group consisting of:
2-(dimethylamino)ethyl 7-({5-[4-(5-methyl-1H-1,2,3-triazol-1-yl)phenyl]pyrimidin-2-yl}amino)-1H,2H,3H-pyrido[2,3-b][1,4]oxazine-1-carboxylate;
2-(dimethylamino)ethyl 7-({5-[4-(dimethylcarbamoyl)phenyl]-4-methoxypyrimidin-2-yl}amino)-1H,2H,3H-pyrido[2,3-b][1,4]oxazine-1-carboxylate;
1-{4-[2-({1-[2-(dimethylamino)acetyl]-1H,2H,3H-pyrido[2,3-b][1,4]oxazin-7-yl}amino)-4-methoxypyrimidin-5-yl]phenyl}pyrrolidin-2-one;
2-(dimethylamino)-1-[7-({5-[4-(5-methyl-1H-1,2,3-triazol-1-yl)phenyl]pyrimidin-2-yl}amino)-1H,2H,3H-pyrido[2,3-b][1,4]oxazin-1-yl]ethan-1-one;
2-(diethylamino)ethyl 7-[(5-{4-[(2R)-2-methyl-5-oxopyrrolidin-1-yl]phenyl}pyrimidin-2-yl)amino]-1H,2H,3H-pyrido[2,3-b][1,4]oxazine-1-carboxylate;
2-(diethylamino)ethyl 7-({5-[4-(2-oxopyrrolidin-1-yl)phenyl]pyrimidin-2-yl}amino)-1H,2H,3H-pyrido[2,3-b][1,4]oxazine-1-carboxylate;
N-[2-(diethylamino)ethyl]-7-[(4-methoxy-5-{4-[(2R)-2-methyl-5-oxopyrrolidin-1-yl]phenyl}pyrimidin-2-yl)amino]-N-methyl-1H,2H,3H-pyrido[2,3-b][1,4]oxazine-1-carboxamide;
N-[2-(diethylamino)ethyl]-N-methyl-7-[(5-{4-[(2R)-2-methyl-5-oxopyrrolidin-1-yl]phenyl}pyrimidin-2-yl)amino]-1H,2H,3H-pyrido[2,3-b][1,4]oxazine-1-carboxamide;
1-{4-[2-({1-[2-(diethylamino)ethyl]-1H,2H,3H-pyrido[2,3-b][1,4]oxazin-7-yl}amino)-4-methoxypyrimidin-5-yl]phenyl}pyrrolidin-2-one; and
N-[2-(diethylamino)ethyl]-7-[(5-{4-[(2R)-2-methyl-5-oxopyrrolidin-1-yl]phenyl}pyrimidin-2-yl)amino]-1H,2H,3H-pyrido[2,3-b][1,4]oxazine-1-carboxamide.

5. A pharmaceutical composition comprising a compound of claim 1, and a pharmaceutically acceptable carrier.

6. A method of inhibiting PI5P4K comprising administering to a patient in need thereof an effective amount of a compound of claim 1.

7. The method of claim 6, wherein the patient is selected for treatment based on either (i) gene amplification and/or elevated tumor expression of PI5P4K; or (ii) tumor expression of p53 mutations.

8. The method of claim 7, wherein the patient is selected for treatment based on gene amplification and/or elevated tumor expression of PI5P4K, and wherein the gene amplified and/or expressed is PI5P4Kα gene, PI5P4Kβ gene, or PI5P4Kγ gene.

9. The method of claim 6, wherein administration of the compound induces a change in the cell cycle or cell viability.

10. A method of inducing cell cycle arrest, apoptosis in tumor cells, and/or enhanced tumor specific T-cell immunity, comprising contacting the cells with an effective amount of a compound of claim 1.

11. The compound of claim 1, wherein $R_1$ is —N($R_2$)C(O)$R_3$.

12. The compound of claim 11, wherein $R_2$ and $R_3$ are taken together with the atom to which they are each attached to form a heterocycle optionally substituted with one or more $R_4$.

13. The compound of claim 12, wherein $R_4$ is methyl.

14. The compound of claim 1, wherein $X_2$ is N.

15. The compound of claim 1, wherein $R_{15}$ is —C(O)O$R_{23}$.

* * * * *